US009025027B2

(12) United States Patent
Xue et al.

(10) Patent No.: US 9,025,027 B2
(45) Date of Patent: May 5, 2015

(54) OBJECT IDENTIFICATION DEVICE, MOVING OBJECT CONTROLLING APPARATUS HAVING OBJECT IDENTIFICATION DEVICE, INFORMATION PRESENTING APPARATUS HAVING OBJECT IDENTIFICATION DEVICE, AND SPECTROSCOPIC IMAGE CAPTURING APPARATUS

(75) Inventors: Li Xue, Kanagawa (JP); Hideaki Hirai, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 497 days.

(21) Appl. No.: 13/230,009

(22) Filed: Sep. 12, 2011

(65) Prior Publication Data

US 2012/0069181 A1    Mar. 22, 2012

(30) Foreign Application Priority Data

Sep. 16, 2010  (JP) .................................. 2010-208415
Oct. 27, 2010  (JP) .................................. 2010-241084
Jul. 13, 2011  (JP) .................................. 2011-154695

(51) Int. Cl.
*H04N 7/18*     (2006.01)
*G08G 1/16*     (2006.01)
(Continued)

(52) U.S. Cl.
CPC ................ *G08G 1/16* (2013.01); *G01J 3/0229* (2013.01); *G01J 3/28* (2013.01); *G01J 3/447* (2013.01);
(Continued)

(58) Field of Classification Search
USPC ....................................................... 348/148
See application file for complete search history.

(56) References Cited

U.S. PATENT DOCUMENTS 8,165,421 B2 *   4/2012  Choi et al. .................... 382/275
2005/0030305 A1 *   2/2005  Brown et al. ................. 345/207
(Continued)

FOREIGN PATENT DOCUMENTS

EP    2136198 A1 * 12/2009 ............. G01N 21/21
JP    61-84605    4/1986
(Continued)

OTHER PUBLICATIONS

The Extended European Search Report issued Oct. 4, 2012, in Application No. / Patent No. 11180655.0-2217 / 2439716.
(Continued)

*Primary Examiner* — Richard Torrente
(74) *Attorney, Agent, or Firm* — Oblon, McClelland, Maier & Neustadt, L.L.P.

(57) ABSTRACT

An object identification device includes an image capturing device to capture images polarized in different directions. A noise removal unit removes noise in the polarized images using a noise removing parameter. An index value computing unit computes an object identification index value for identification-processing areas in the polarized images using data of noise-removed polarized images. An object identification processing unit conducts object identification by determining identification processing areas corresponding to an identification target object based on the object identification index value. An environment information obtaining unit obtains environment information. An environmental condition determination unit determines an environmental condition based on the environment information. A parameter storage unit stores noise removing parameters prepared for mutually exclusive environmental conditions. The noise removal unit reads a noise removing parameter from the parameter storage unit to conduct noise removal. A method of identifying an object and a spectroscopic image capturing apparatus are also provided.

12 Claims, 25 Drawing Sheets

(51) Int. Cl.
  *G01J 3/02* (2006.01)
  *G01J 3/28* (2006.01)
  *G01J 3/447* (2006.01)
  *G01J 3/453* (2006.01)
  *G01J 9/02* (2006.01)
  *G01N 21/31* (2006.01)
  *G06K 9/00* (2006.01)
  *G06K 9/20* (2006.01)
  *G06T 5/00* (2006.01)
  *G06T 5/50* (2006.01)

(52) U.S. Cl.
  CPC ............... *G01J 3/453* (2013.01); *G01J 9/0246* (2013.01); *G01N 21/314* (2013.01); *G06K 9/00798* (2013.01); *G06K 9/00825* (2013.01); *G06K 9/2018* (2013.01); *G06T 5/002* (2013.01); *G06T 5/50* (2013.01); *G06K 9/00805* (2013.01)

(56) References Cited

U.S. PATENT DOCUMENTS

| | | | |
|---|---|---|---|
| 2010/0013979 A1 | 1/2010 | Golub et al. | |
| 2011/0169943 A1* | 7/2011 | Bachman et al. | 348/117 |

FOREIGN PATENT DOCUMENTS

| | | |
|---|---|---|
| JP | 11-175702 | 7/1999 |
| JP | 2004-299443 | 10/2004 |
| JP | 2005-31007 | 2/2005 |
| JP | 2005-57541 | 3/2005 |
| JP | 4183542 | 9/2008 |
| JP | 4183542 * | 11/2008 |
| JP | 2009-25198 | 2/2009 |
| JP | 2010-171753 | 8/2010 |
| JP | 2011-150688 | 8/2011 |
| WO | WO 2006/111911 A2 | 10/2006 |
| WO | WO 2006/111911 A3 | 10/2006 |
| WO | WO 2008/012812 A2 | 1/2008 |
| WO | WO 2008/012812 A3 | 1/2008 |
| WO | WO 2008/097562 A1 | 8/2008 |
| WO | WO 2010/082455 A1 | 7/2010 |

OTHER PUBLICATIONS

Partial European Search Report issued Feb. 15, 2012, in Patent Application No. 11180655.0.

Susumu Moriya, "Latest two-dimensional spectrometric equipment. Imaging spectroscope "ImSpector". Basic characteristics and the application.", Optical Alliance, vol. 10, Nov. 1999, 7 Pages. (with English Abstract).

Japanese Office Action issued May 16, 2014, in Japan Patent Application No. 2010-241084.

* cited by examiner

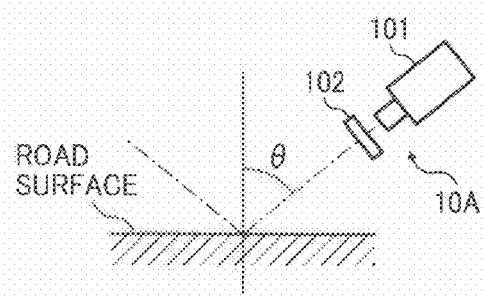
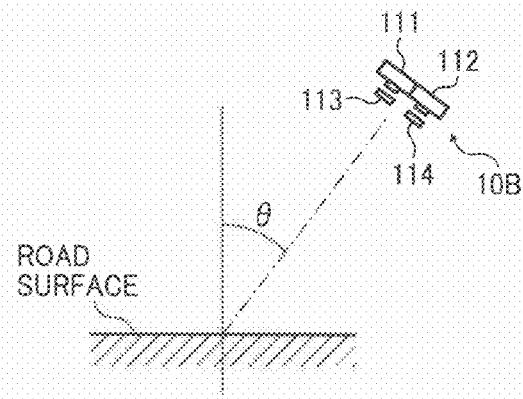
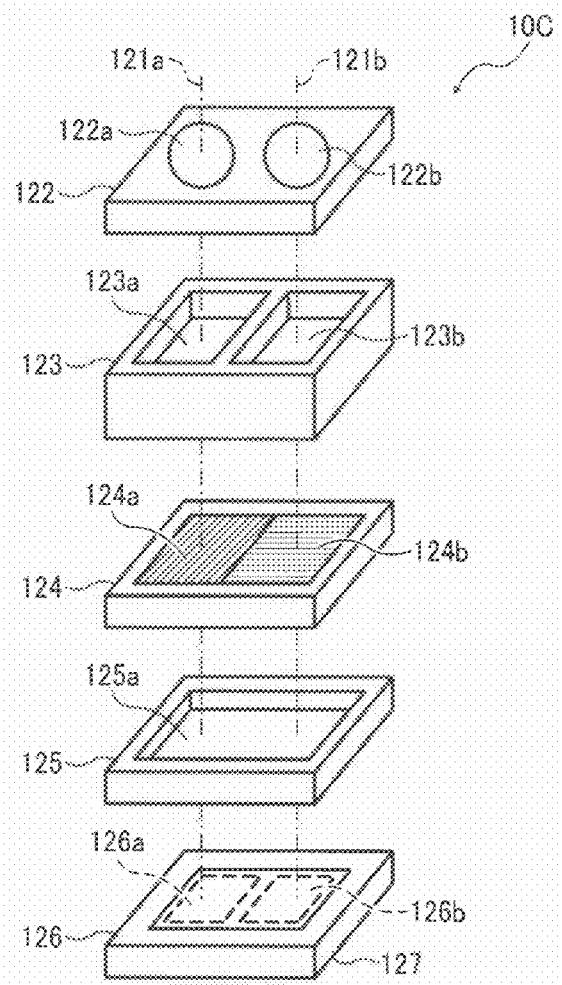

FIG. 11
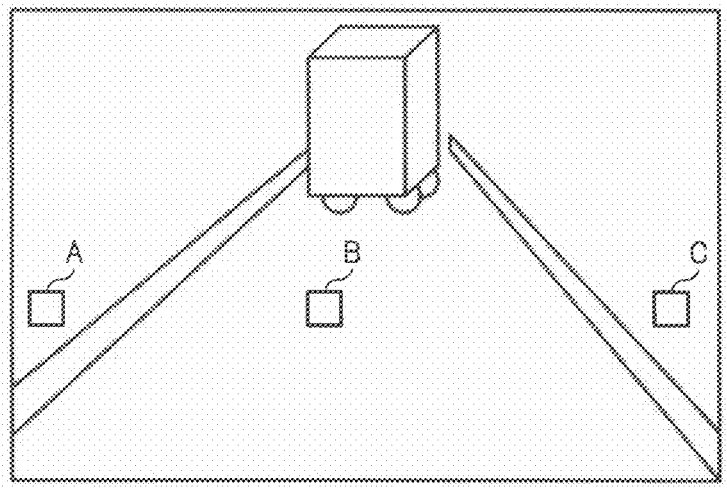
FIG. 12
(a)
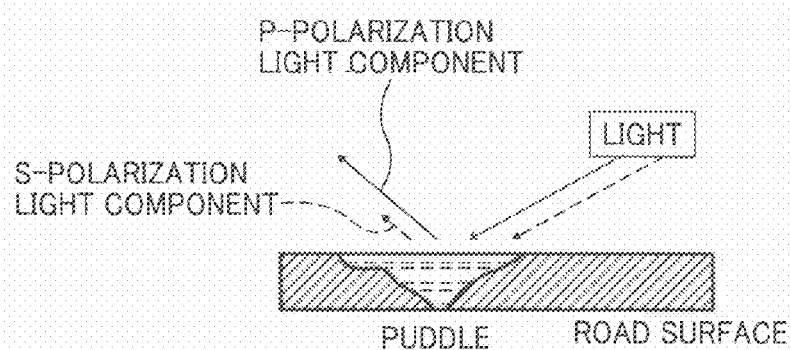
(b)
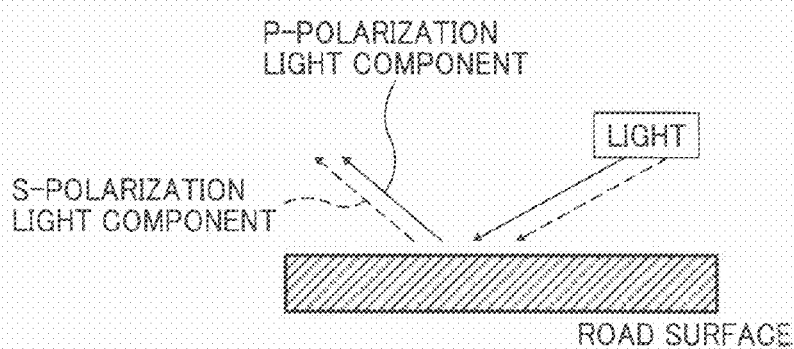

(a) 450nm  (b) 550nm  (c) 650nm

OBJECT IDENTIFICATION DEVICE, MOVING OBJECT CONTROLLING APPARATUS HAVING OBJECT IDENTIFICATION DEVICE, INFORMATION PRESENTING APPARATUS HAVING OBJECT IDENTIFICATION DEVICE, AND SPECTROSCOPIC IMAGE CAPTURING APPARATUS

CROSS-REFERENCE TO RELATED APPLICATIONS

This application claims priority to Japanese Patent Application Nos. 2010-208415, filed on Sep. 16, 2010, 2010-241084, filed on Oct. 27, 2010, and 2011-154695, filed on Jul. 13, 2011, respectively, the disclosures of which are incorporated by reference herein in their entirety.

BACKGROUND OF THE INVENTION

1. Field of the Invention

The present invention relates to an object identification device to identify objects existing in an image capturing area, a moving object controlling apparatus to conduct a movement control of moving vehicles such as automobiles, ships, airplanes, and industrial robots using an identification result of the object identification device, and an information presenting apparatus to present useful information to operators of the moving vehicles. Further, the present invention relates to a spectroscopic image capturing apparatus to obtain a two-dimensional spectroscopic image, in which wavelength information is correlated to each point in an image capturing area.

2. Description of the Background Art

Object identification devices are widely employed for moving object control apparatuses to control moving vehicles such as automobiles, ships, airplanes, and industrial robots, and for information presenting apparatuses to present useful information to operators of moving vehicles. Specifically, for example, the object identification devices are employed for a driver support system such as adaptive cruise control (ACC) to reduce burden on operators of vehicles.

Such vehicle driving support systems implement an automatic braking and warning to evade obstacles and to reduce the shock of impact in the event of a collision; vehicle speed adjustment to maintain the vehicle-to-vehicle distance with a vehicle ahead; and driving assist to prevent a vehicle from straying out of its lane. Such vehicle driving support systems must be able to effectively differentiate, and recognize or identify, objects such as obstacles existing around one vehicle, another vehicle in front of one vehicle (in-front vehicle, hereinafter), lane markings, and the like.

Hitherto, several object identification devices have been disclosed. For example, JP-H11-175702-A discloses an object identification device that identifies objects such as lane markings, in which lines in a captured image of roads are detected to detect a change in relative position of a vehicle such as an automobile with respect to traffic lanes as defined by lane markings such as white-painted lines or white lines.

In general, when puddles of water are present on a road due to rainy weather, sunlight reflected off the puddles as specular reflection may be captured with a same light intensity as that of the lane markings (e.g., the white lines) on the road and misidentified as lane markings. The object identification device is used to solve such problem.

Specifically, the effect of puddles is removed from the road image before conducting white line identification processing by removing a specular reflection component (i.e., noise component) from the captured road image, after which the white lines are recognized using the scattered light component. The specular reflection component can be removed by taking advantage of the fact that the horizontal polarized component of the specular reflection has a Brewster's angle of substantially zero, and the scattered light component has substantially the same level of vertical polarized component and horizontal polarized component. A difference between the vertical polarized component and the horizontal polarized component included in the captured road image is computed and a correction coefficient dependent on an angle of incidence included in the horizontal polarized component is multiplied by the computed difference to a compute specular reflection component. The computed specular reflection component is then subtracted from the horizontal polarized component to obtain a scattered light component image from which only the specular reflection component is removed from the road image.

JP-2004-299443-A discloses a road condition detector to detect whether a road surface is wet or dry. A captured image of the road surface includes a vertical polarized component of a vertical polarized image and a horizontal polarized component of a horizontal polarized image. A ratio of the polarized components is computed as a polarized light intensity ratio. Based on the computed polarized light intensity ratio, the road condition detector detects a road surface condition. The road condition detector uses a moving average method to reduce the effect of changes in ambient lighting occurring while the vehicle is moving, the effect of noise caused by the installation angle of a vehicle-mounted camera to compute a polarized light intensity ratio can be computed by reducing noise.

Similar to JP-2004-299443-A, JP-2009-25198-A discloses a road condition detector to detect whether a road surface is wet or dry, in which a noise removing device removes noise caused by incident light intermittently emitted by streetlamps/streetlights. The road condition detector can obtain road surface images having less effect of the streetlamps/streetlights. Based on a ratio of vertical polarized components and horizontal polarized components of the obtained images and a difference between vertical polarized components and horizontal polarized components of the obtained images, the road condition detector can detect whether the road surface is wet or dry.

Conventional object identification devices identify identification target objects, such as obstacles on road surfaces, in a captured image area using a difference in light intensity observed in the captured image area. Specifically, the object identification device extracts boundaries or edges of an identification target object and then identifies the identification target object, defined by the edges, in the captured image area. The identification target objects may be road side-end obstacles such as side walls, guardrails/crash barriers, telegraph poles/utility poles, streetlamps/streetlights, stepped portions such as pedestrian crossings at the road side-end, in-front vehicles, lane markings, or the like.

However, the above-described method may have a problem if the captured image includes a noise component, which degrades the precision of light intensity data used for identifying objects. For example, if no objects such as lane markings exist on a road surface but a high light intensity portion of road surface having a light intensity too great compared to other portions of the road surface exists on the road surface, the object identification device may extract boundaries of such portions as edges of an object, and then misidentify such portion of the road surface as an object existing on the road surface such as lane markings. When such misidentification occurs, the adaptive cruise control (ACC) misidentifies a shaded portion at a road side-end as an obstacle such as a side wall and initiates erroneous control or erroneous processing in the form of an evasive maneuver or the like.

JP-2011-150688-A discloses a method of identifying three-dimensional objects on a road surface. Each of two polarized images captured by an image capturing device is divided into a plurality of processing areas. For each processing area, a total light intensity of the two polarized images and a difference in light intensity between the two polarized images are computed, and then a polarization intensity difference, which is a ratio of the difference of light intensity with respect to the total light intensity, is computed to identify three-dimensional objects on the road surface. Specifically, based on the computed polarization intensity difference, the processing areas corresponding to the identification target object are determined, and a plurality of processing areas, which are close to each other and determined as the processing areas corresponding to the identification target object, are identified as an image area of identification target object.

In the conventional method, when a difference of light intensity in a captured image is not so great, the identification precision may deteriorate. The method in described in JP-2011-150688-A can identify three-dimensional objects in a captured image with a high precision even if the difference of light intensity in the captured image is not so great.

An object identification method using a difference in light intensity in the captured image and the three-dimensional object identification method using the polarization intensity difference may not identify an image area of identification target object in a captured image with high precision if some light intensity information such as noise component exists in the captured image, because such noise component degrades the precision of identification of the target object. Such noise component can be removed from captured images using conventional noise removing methods using noise removing parameters, and the object identification processing is conducted using captured images after conducting the noise removing processing on the captured images.

However, conventional noise removing methods cannot remove noise components from captured images effectively when environmental conditions of objects in image capturing areas differs such as fine weather vs. rainy weather, sunny place vs. shade place, difference of light angle irradiated on an object, or the like. Such problem occurs not only for the object identification devices for the driver support system, but also for the object identification devices used for other fields such as robot control.

Further, spectroscopes are widely used to obtain an optical spectrum. Typical, spectroscopes use a prism or a diffraction grating to decompose the incident light into a plurality of wavelength components, and the light intensity of wavelength components is detected by a light receiving element. However, the typical spectroscope cannot correlate positional information of incident light with the optical spectrum of incident light.

Recently, spectroscopic image capturing apparatuses that can capture a two-dimensional spectroscopic image have been developed, in which each point in an image capturing area can be correlated with the wavelength of the light measured at each point. Such spectroscopic image expresses the two-dimensional distribution of wavelengths at each point in the image capturing area, and the wavelength components at each point can be expressed, for example, as a difference in gradation in the image capturing area. The optical spectrum can be obtained with a wavelength selection filter such as a band pass filter and a low pass/high pass filter, by a dispersive element such as a prism and diffraction grating, and by the Fourier-transform spectroscopy. Spectroscopic image capturing apparatuses using such methods to obtain the optical spectrum have been developed.

Spectroscopic image capturing apparatuses using such methods to obtain the optical spectrum have been developed. For example, JP-2005-57541-A discloses a spectroscopy camera head unit using a wavelength selection filter to capture a spectroscopic image. In the spectroscopy camera head unit, a two-dimensional image capturing element receives incident light from a photographic subject via the wavelength selection filter, and a spectroscopic image of wavelength components matched to the wavelength selection filter is obtained. The spectroscopy camera head unit uses a liquid crystal wavelength tunable filter (LCTF) as the wavelength selection filter to dynamically switch wavelength that can pass the filter. Therefore, by capturing images while switching passable wavelength of the wavelength selection filter, a plurality of images captured using different wavelength components can be obtained. By synthesizing such images, a two-dimensional spectroscopic image that correlates each point in an image capturing area with wavelength components of light measured at each point can be obtained.

A non-patent reference (pages 4-9, November 1999, "Optical Alliance", JAPAN INDUSTRIAL PUBLISHING CO., LTD) discloses a planar spectrometric system using a dispersive element that can capture a spectroscopic image. The planar spectrometric system employs imaging spectroscopy that simultaneously measures positional information and spectrum information at multiple points arranged in a straight line to obtain a spectroscopic image. The imaging spectroscopy captures images by scanning in a direction perpendicular to the arrangement direction of the multiple points, by which a two-dimensional spectroscopic image, which correlates each point in an image capturing area with wavelength of light measured at each point can be obtained.

JP-2005-31007-A discloses a spectral instrument using Fourier-transform spectroscopy. In this spectral instrument, the incident light is split into two light paths or two polarized components and one of the light paths or polarized components is given a certain phase difference that causes the two light paths or two polarized components to interfere with each other to generate detection signals. The detection signals are Fourier-transformed by a computer to obtain an optical spectrum. The spectral instrument can obtain a spectroscopic image by conducting detection while changing the phase difference set for the two light paths or two polarized components, perpendicular to each other, by which a two-dimensionally distributed optical spectrum for a given wavelength range can be obtained.

However, the above methods need a long processing time to obtain the spectroscopic image, and therefore such methods may not be suitable to capturing the spectroscopic image in real time at high speed. Specifically, when the wavelength selection filter is used, one image-capturing action can obtain a two-dimensional spectroscopic profile only for one wavelength component. Therefore, to obtain a two-dimensional spectroscopic image for a plurality of wavelengths, a plurality of images for different wavelength components needs to be captured and then synthesized. These operations take time, thereby lengthening the processing time required for obtaining the spectroscopic image. Such lengthening of the processing time may occur similarly when the dispersive element and Fourier-transform spectroscopy are used.

In general, spectroscopic images generated by using the image difference captured by a spectroscopic image capturing apparatus include a noise component. The difference between any two adjacent areas in the spectroscopic image can be expressed as a difference in gradient. The received light intensity of the two adjacent areas is measured and compared. If the received light intensity in one of the adjacent areas becomes too great compared to the received light intensity in the other one of the adjacent areas, such difference can be identified as noise because such a great difference does not usually occur in adjacent areas, which receive light at adjacent points in an image capturing area. If such noise information is included in a spectroscopic image, the spectroscopic image may not be processed correctly subsequently. For example, when the object identification process to recognize edge portions in the spectroscopic image as a contour of object is conducted, the noise in the spectroscopic image may be extracted as an edge portion of object, thereby degrading object identification precision.

SUMMARY

In one aspect of the invention, an object identification device is devised. The object identification device includes: an image capturing device to receive polarized light polarized in two different directions included in light reflected from an object in an image capturing area and capture two polarized images, one polarized image for each type of polarized light; a noise removal unit to remove a noise component included in each of the two polarized images captured by the image capturing device, using a noise removing parameter; an index value computing unit to divide each of the two polarized images captured by the image capturing device into identification-processing areas to compute an object identification index value for each of the identification-processing areas using light intensity data of each of the two polarized images from which the noise component is removed by the noise removal unit; an object identification processing unit that conducts an object identification process that determines a plurality of identification processing areas corresponding to an identification target object based on the object identification index value of each of the identification processing areas computed by the index value computing unit, and identifies a plurality of adjacent identification processing areas as the identification processing areas corresponding to the identification target object as an image area of the identification target object; an environment information obtaining unit to obtain environment information to determine an environmental condition of an object in an image capturing area; an environmental condition determination unit to determine an environmental condition of the object in the image capturing area based on the environment information obtained by the environment information obtaining unit; and a parameter storage unit to store one or more noise removing parameters to remove a noise component included in the two polarized images captured under an environmental condition determined by the environmental condition determination unit, each noise removing parameter being prepared and stored for one of a plurality of mutually exclusive environmental conditions. The noise removal unit reads out a noise removing parameter for the environmental condition determined by the environmental condition determination unit from the parameter storage unit, and conducts the noise removing process using the noise removing parameter.

In another aspect of the invention, a method of identifying an object is devised. The method of identifying an object includes the steps of: receiving light polarized in two different polarization directions included in light reflected from an object in an image capturing area using an image capturing device and capturing a polarized image for each of the two types of polarized light using the image capturing device; dividing each of the two polarized images captured by the image capturing device into identification processing areas to compute an object identification index value for each of the identification processing areas using an index value computing unit using light intensity data of each of the two polarized images from which the noise component has been removed by the noise removal unit; determining identification processing areas corresponding to an identification target object using an object identification processing unit based on the object identification index value of each of the identification processing areas computed by the index value computing unit; conducting an object identification process in which the object identification processing unit identifies a plurality of adjacent identification processing areas determined as the identification processing areas corresponding to the identification target object as an image area of the identification target object; obtaining environment information to determine an environmental condition of an object in the image capturing area using an environment information obtaining unit; determining an environmental condition of the object existing in the image capturing area based on the environment information obtained by the environment information obtaining unit; storing a plurality of noise removing parameters in a parameter storage unit, each of the noise removing parameters being prepared and stored for a plurality of mutually exclusive environmental conditions; reading out one noise removing parameter from among the plurality of noise removing parameters stored in the parameter storage unit for the environmental condition determined by the environmental condition determination unit to remove a noise component included in the two polarized images captured under the environmental condition; and removing the noise component included in the two polarized images captured under the environmental condition determined by the environmental condition determination unit using the noise removing parameter read from the parameter storage unit.

In another aspect of the invention, a spectroscopic image capturing apparatus for obtaining a two-dimensional spectroscopic image correlating each point in an image capturing area with wavelength information measured at each point is devised. The spectroscopic image capturing apparatus includes an optical filter; an image sensor having a two-dimensionally arranged pixel array to receive and detect light from an image capturing area via the optical filter and output a detection result, in which the optical filter includes a diffraction grating having a grid pattern, in which one grid area corresponds to one unit area defined on the image sensor, the one unit area being composed of one or more pixels; an image generator to generate a difference-value-based image based on a difference value between received light intensity of one unit area and received light intensity of another adjacent unit area, the difference value computable based on the detection result of the image sensor, in which an interference level on the image sensor changes at each point depending on a diffraction angle of light passing the diffraction grating; and a noise removal unit to remove a noise component included in the difference-value-based image generated by the image generator using a noise removing parameter.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 2 shows one configuration of polarized light camera useable for the operator support system of FIG. 1;

FIG. 3 shows another configuration of polarized light camera useable for the operator support system of FIG. 1;

FIG. 4 shows another configuration of polarized light camera useable for the operator support system of FIG. 1;

FIG. 11 shows a schematic example of captured image;

FIG. 12(a) shows an expanded view of a road surface at wet condition, and FIG. 12(b) shows an expanded view of a road surface at dry condition;

Figure 1:
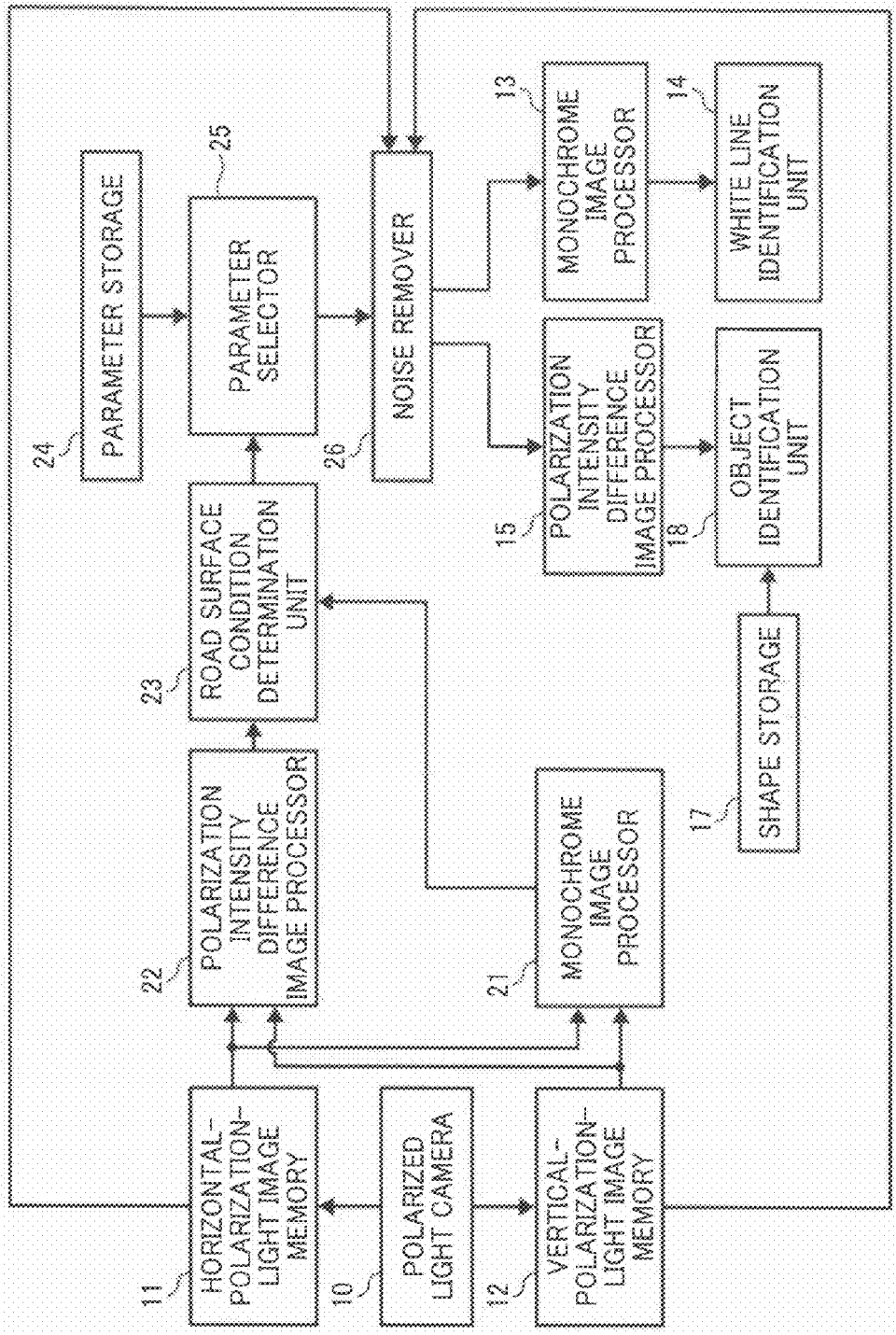
FIG. 1 shows a functional block diagram of an operator support system according to an example embodiment.

The accompanying drawings are intended to depict exemplary embodiments of the present invention and should not be interpreted to limit the scope thereof. The accompanying drawings are not to be considered as drawn to scale unless

DETAILED DESCRIPTION OF EXEMPLARY EMBODIMENTS

A description is now given of exemplary embodiments of the present invention. It should be noted that although such terms as first, second, etc. may be used herein to describe various elements, components, regions, layers and/or sections, it should be understood that such elements, components, regions, layers and/or sections are not limited thereby because such terms are relative, that is, used only to distinguish one element, component, region, layer or section from another region, layer or section. Thus, for example, a first element, component, region, layer or section discussed below could be termed a second element, component, region, layer or section without departing from the teachings of the present invention.

In addition, it should be noted that the terminology used herein is for the purpose of describing particular embodiments only and is not intended to be limiting of the present invention. Thus, for example, as used herein, the singular forms "a", "an" and "the" are intended to include the plural forms as well, unless the context clearly indicates otherwise. Moreover, the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Furthermore, although in describing views shown in the drawings, specific terminology is employed for the sake of clarity, the present disclosure is not limited to the specific terminology so selected and it is to be understood that each specific element includes all technical equivalents that operate in a similar manner.

Referring now to the drawings, an apparatus, a system, or a method according to example embodiment is described hereinafter, wherein the apparatus, method, or system can be used with a network.

A description is now given of an operator support system used with an object identification device according to an example embodiment, in which a boundary of identification target object on a road surface or road side-end obstacles can be identified as a white line edge portion or a road side-end edge portion, and the operator support system can be used to reduce a burden on operators of vehicle such as automobile based on the identification result of the object identification device. The operator support system may be used as a driver support system for an automobile driving, but not limited thereto.

In example embodiments, a noise removing processing can be conducted by using noise removing parameters matched to the road surface conditions such as weather conditions or environmental conditions, which may be a dry condition, a wet condition, a snowed condition, or the like. With such a configuration, the object identification can be conducted with a high precision for various weather conditions.

FIG. 1 shows a functional block diagram of a operator support system according to an example embodiment. A vehicle such as an automobile can be mounted with an image capturing device such as a polarized light camera 10. The polarized light camera 10 captures images of scenes around the vehicle such as an automobile, which is a moving object that is moving on a road or the like. Specifically, the polarized light camera 10 can capture images of scenes around the automobile such as a road surface (moving face) that the automobile is running.

The polarized light camera 10 can capture RAW image data of polarized light for each of processing areas of pixels, in which RAW image data of polarized light includes vertical-polarization light intensity (hereinafter, S-polarization light intensity) and horizontal-polarization light intensity (hereinafter, P-polarization light intensity).

The horizontal-polarization image data obtained from the P-polarization light intensity data included in the RAW image data of polarized light is stored in a horizontal-polarization image memory 11. The vertical-polarization image data obtained from the S-polarization light intensity data included in the RAW image data of polarized light is stored in a vertical-polarization image memory 12. These image data are then transmitted to a monochrome image processor 21, a polarization intensity difference image processor 22, and a noise remover 26. Such processing units and other processing units to be described later may be devised as controllers configured with using various types of processors, circuits, or the like such as a programmed processor, a circuit, an application specific integrated circuit (ASIC), used singly or in combination.

The polarized light camera 10 includes an image capturing element such as a charge-coupled device (CCD), a complementary metal oxide semiconductor (CMOS) used as a light receiving element, with which surrounding environment images can be captured, for example, as pixel images with a mega pixel size. Preferably, the polarized light camera 10 consecutively captures the surrounding environment images with a short time interval so that images can be captured in real time as much as possible.

The polarized light camera 10 may be mounted, for example, at a rear-view mirror of automobile to capture scenes viewable in front of one automobile, which may be a front view from one automobile including the road surface. Further, the polarized light camera 10 may be mounted, for example, at a side mirror to capture scenes at a lateral side of automobile. Further, the polarized light camera 10 may be mounted, for example, at a back side of automobile such as trunk side of automobile to capture scenes at a back side of automobile. In an example embodiment, the polarized light camera 10 may be mounted, for example, at the rear-view mirror of automobile to capture scenes viewable in front of automobile such as a front view including the road surface.

FIG. 2 shows one configuration of the polarized light camera 10, referred to as a polarized light camera 10A. As shown in FIG. 2, the polarized light camera 10A includes a camera 101 and a rotatable polarizer 102, in which the camera 101 includes an image capturing element such as CCD, and the rotatable polarizer 102 is disposed in front of the camera 101, wherein the rotatable polarizer 102 can be rotated in a given direction.

As for the polarized light camera 10A, the polarization direction of light passing the rotatable polarizer 102 changes depending on a rotating angle of the rotatable polarizer 102. Therefore, the camera 101 can capture the P-polarization image and S-polarization image alternatively by rotating the rotatable polarizer 102.

FIG. 3 shows another configuration of polarized light camera 10, referred to as a polarized light camera 10B. As shown in FIG. 3, the polarized light camera 10B includes two cameras 111 and 112 including an image capturing element such as CCD, a S-polarized light filter 113 to pass through S-polarized light, and a P-polarized light filter 114 to pass through P-polarized light. The S-polarized light filter 113 is disposed in front of the camera 111, and the P-polarized light filter 114 in front of the camera 112.

As for the polarized light camera 10A shown in FIG. 2, because a single camera (i.e., camera 101) captures the P-polarized image and S-polarized image alternatively, the polarized light camera 10A cannot capture the P-polarized image and S-polarized image simultaneously. In contrast, the polarized light camera 10B shown in FIG. 3 can capture the P-polarized image and S-image simultaneously.

FIG. 4 shows another configuration of the polarization light camera 10, referred to as a polarized light camera 10C. As shown in FIG. 4, the polarized light camera 10C includes an image capturing element for P-polarized image and an image capturing element for S-polarized image as similar to the polarized light camera 10B shown in FIG. 3. However, each of image capturing elements is disposed close to each other in the polarized light camera 10C when compared with the polarized light camera 10B shown in FIG. 3. Therefore, the polarized light camera 10C can be configured smaller than the polarized light camera 10B shown in FIG. 3.

As shown in FIG. 4, the polarized light camera 10C includes a lens array 122, a light shield spacer 123, a polarization filter 124, a spacer 125, and an image capturing unit 126, which are stacked one to another.

The lens array 122 includes two image capture lenses 122a and 122b. Each of the image capture lenses 122a and 122b is a single lens such as an aspherical lens having a same shape. The image capture lenses 122a and 122b are disposed on a same face while the optical axis 121a/121b of image capture lenses 122a/122b are parallel to each other.

The light shield spacer 123 has two openings 123a and 123b, which is disposed at an opposite side of a photographic subject with respect to the lens array 122. Each of the openings 123a and 123b has a given size, and the optical axis 121a and the optical axis 121b pass through the center of each of the openings 123a and 123b, wherein the interior face of the openings 123a and 123b is treated with an anti-reflection treatment such as black painting, rough face, matting, or the like.

The polarization filter 124 is a polarization filter of area divided type having two polarization areas 124a and 124b, in which, for example, the polarization face of polarization area 124a and the polarization face of polarization area 124b are different for ninety degrees for polarization. The polarization areas 124a and 124b are disposed at an opposite side of the lens array 122 with respect to the light shield spacer 123. When non-polarized light, which is an electromagnetic wave oscillating in any directions, passes the polarization areas 124a and 124b, the polarization areas 124a and 124b pass through waves oscillating in given directions, by which light having polarized along the polarization face can pass the polarization areas 124a and 124b. Further, a polarization filter of area-divided type having a clear boundary can be obtained by using a wire grid made of a metal having fine concave/convex shape, or by a fabrication technology of auto cloning for photonic crystals.

The spacer 125 is has a rectangular frame having an opening 125a corresponding to the polarization areas 124a and 124b of the polarization filter 124, corresponding to a polarized light "a" and a polarized light "b." The spacer 125 is disposed at an opposite side of the light shield spacer 123 with respect to the polarization filter 124.

The image capturing unit 126 includes a base plate 127 and two image capturing elements 126a and 126b disposed on the base plate 127. The image capturing unit 126 is disposed at an opposite side of the polarization filter 124 with respect to the spacer 125. In an example embodiment, a monochrome sensing may be conducted, in which the image capturing elements 126a and 126b do not include color filters. If a color image sensing is to be conducted, the image capturing elements 126a and 126b include color filters.

Figure 5:
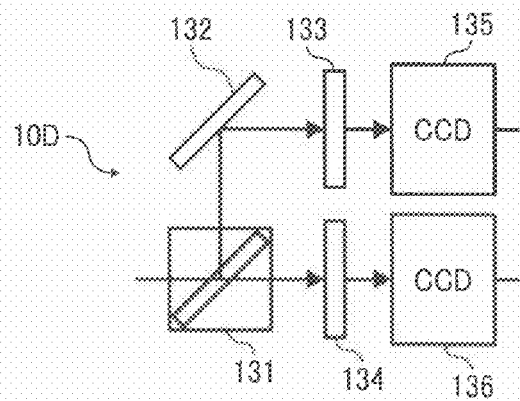
FIG. 5 configuration of polarized light camera useable for the operator support system of FIG. 1.

FIG. 5 shows another configuration of the polarized light camera 10 referred to as a polarized light camera 10D. As shown in FIG. 5, the polarized light camera 10D includes a half mirror 131 having 1-to-1 light passing performance, a reflection mirror 132, a S-polarization light filter 133, a P-polarization light filter 134, a S-polarization light CCD 135 to receive S-polarized light via the S-polarization light filter 133, and a P-polarization light CCD 136 to receive P-polarized light via the P-polarization light filter 134.

The polarized light camera 10B (FIG. 3) and the polarized light camera 10C (FIG. 4) can capture S-polarized image and P-polarized image simultaneously, but parallax occurs when capturing images. In contrast, the polarized light camera 10D (FIG. 5) can capture S-polarized image and P-polarized image simultaneously using a same lens, by which parallax does not occur when capturing images, and thereby a correction process for parallax deviation is not required.

Further, instead of the half mirror 131, a prism such as a polarized beam splitter that can reflect P-polarized light and pass through S-polarized light can be used. By using the polarized beam splitter, the S-polarization light filter 133 and P-polarization light filter 134 can be omitted, and the optical system can be simplified, and light use efficiency can be enhanced.

Figure 6:
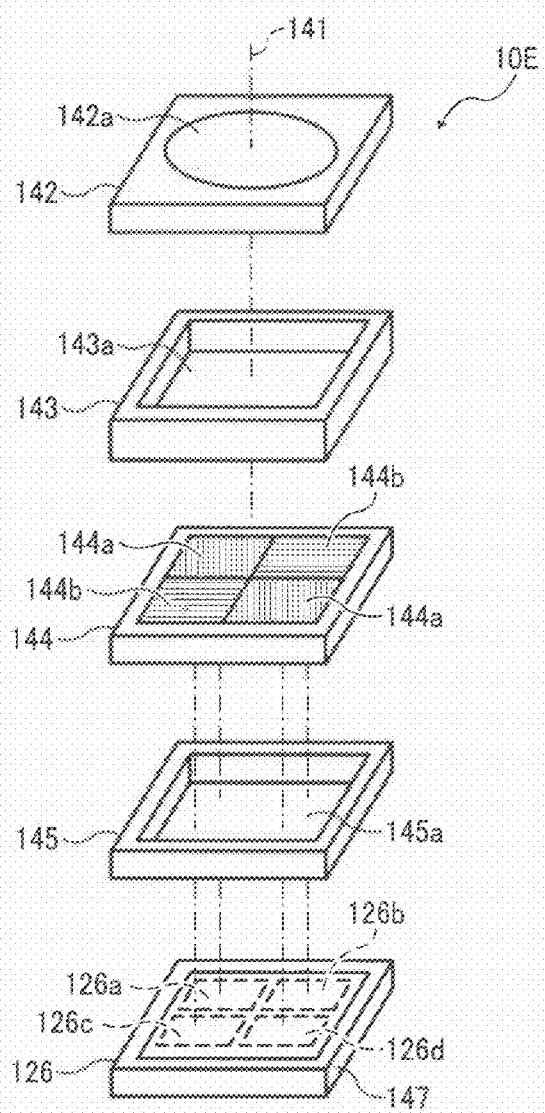
FIG. 6 shows another configuration of polarized light camera useable for the operator support system of FIG. 1.

FIG. 6 shows another configuration of the polarized light camera 10 referred to as a polarized light camera 10E. As shown in FIG. 6, the polarized light camera 10E includes a plurality of units stacked one to another along the light axis as similar to the polarized light camera 10C shown in FIG. 4. However, the polarized light camera 10E uses a single lens such as to capture S-polarized image and P-polarized image. Specifically, the polarized light camera 10E uses an image capture lens 142a as the single lens. The image capture lens 142a can be composed of a plurality of lenses stacked along the light axis.

As similar to the polarized light camera 10D shown in FIG. 5, the polarized light camera 10E can capture S-polarized image and P-polarized image without causing parallax. Further, the polarization light camera 10E shown in FIG. 6 can be configured smaller than the polarized light camera 10D shown in FIG. 5. Further, the polarized light camera 10E includes a polarization light filter 144 as a polarization light filter of area divided type. Specifically, the polarization light filter 144 includes two areas for polarization area 144a and two areas for polarization area 144b, wherein the polarization face of the polarization area 144a and the polarization face the polarization area 144b is different for ninety degrees for polarization. Therefore, four image capturing elements 126a, 126b, 126c, and 126d are disposed as shown in FIG. 6.

Figure 7:
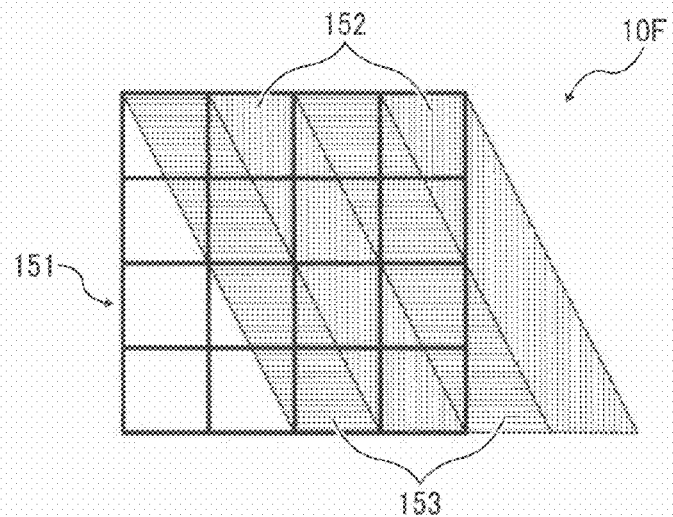
FIG. 7 shows another configuration of polarized light camera useable for the operator support system of FIG. 1.

FIG. 7 shows another configuration of the polarized light camera 10 referred to as a polarized light camera 10F. As shown in FIG. 7, a filter of area divided type is employed. In FIG. 7, each of squares arranged in two directions indicates a light receiving area 151 of a light receiving element, in which a vertical line indicates an area of S-polarization light filter 152, and a horizontal line indicates an area of P-polarization light filter 153. As for the polarized light camera 10F, the light receiving area is not matched to a pixel of light receiving element as 1:1 relationship. For example, the area of the filter 152 (or 153) has a width of one light receiving element in the horizontal direction, and has a length of two light receiving elements in the vertical direction. Therefore, the gradient of boundary of area becomes two, by which a slanted band area is formed by proceeding one pixel in horizontal direction and proceeding two pixels in the horizontal direction.

By combining such filter having a slanted arrangement pattern and a signal processing, even if the positioning precision between the image capturing element and the area divided filter is not so high when bonding each other, S-polarized image and P-polarized image passing the filter can be captured using the filter as a whole. Such polarized light camera can capture S-polarized image and P-polarized image with a reduced cost.

The monochrome image processor 21 computes monochrome image intensity for each pixel using P-polarized light intensity data stored in the horizontal-polarization image memory 11 and S-polarized light intensity data stored in the vertical-polarization image memory 12. Specifically, the monochrome image processor 21 computes a total polarized light intensity for concerned pixels (i.e., P-polarized light intensity+S-polarized light intensity).

The monochrome image intensity data computed by the monochrome image processor 21 is output to the road surface condition determination unit 23 used as an environmental condition determination unit.

The polarization intensity difference image processor 22 computes a polarization intensity difference for each pixel using P-polarized light intensity data stored in the horizontal-polarization image memory 11 and S-polarized light intensity data stored in the vertical-polarization image memory 12.

The polarization intensity difference can be computed by using a following calculation formula (1). The polarization intensity difference is a ratio of a difference of P-polarized light intensity and S-polarized light intensity (difference of light intensity of two polarized lights) with respect to a total of P-polarized light intensity and S-polarized light intensity (total of light intensity of two polarized lights).

Further, the polarization intensity difference can be defined as a difference between P-polarized intensity with respect to the total of light intensity (referred as P-polarization light ratio) and S-polarized intensity with respect to the total of light intensity (referred as S-polarization light ratio). In an example embodiment, the S-polarized light intensity is subtracted from the P-polarized light intensity, but the P-polarized light intensity can be subtracted from the S-polarized light intensity.

Further, instead of the polarization intensity difference, a polarized light ratio computed by using the following calculation formula (2) can be used.

The computed polarization intensity difference computed by the polarization intensity difference image processor 15 is output to the road surface condition determination unit 23.

Polarization intensity difference=(*P*-polarized light intensity−*S*-polarized light intensity)/(*P*-polarized light intensity+*S*-polarized light intensity)    (1)

Polarization light ratio=*P*-polarized light intensity/*S*-polarized light intensity    (2)

The road surface condition determination unit 23 conducts a determination process to determine a road surface condition in an image capturing area using the monochrome image intensity data computed by the monochrome image processor 21, and the polarization intensity difference data computed by the polarization intensity difference image processor 15. The determination process of road surface condition will be described later. The information of road surface condition determined by the road surface condition determination unit 23 is output to a parameter selector 25, which can be used with the noise removal unit.

A parameter storage 24, useable as a parameter storage unit, stores noise removing parameters set for a plurality of environmental conditions such as dry condition, wet condition, and snowed condition, in which noise removing parameters are set for each of environmental conditions while differentiating the noise removing parameters for each of environmental conditions. By using the noise removing parameters, a noise component included in an image captured under each of environmental conditions can be removed with a high precision.

In an example embodiment, as described later, a noise removing method using a $\epsilon$ filter is employed for removing the noise component, in which the noise removing parameter may be referred to $\epsilon$ value. As shown in Table 1 (see below), the parameter storage 24 stores data table, which correlates each of road surface conditions and $\epsilon$ value suitable to each of the road surface conditions.

TABLE 1

| | Road surface condition | Noise removing parameter |
|---|---|---|
| 1 | dry condition | $\epsilon$ for dry condition |
| 2 | wet condition | $\epsilon$ for wet condition |
| 3 | snowed condition | $\epsilon$ for snowed condition |

The $\epsilon$ value suitable or matched to each of road surface conditions can be determined by capturing sample images, for example 100 sample images, for each of the road surface conditions and applying a noise removing filter (i.e., $\epsilon$ filter) in advance. For example, the $\epsilon$ value for dry condition may be suitably set from 45 to 55, and the $\epsilon$ value for wet condition may be suitably set from 60 to 70. The window size of $\epsilon$ filter may be, for example, 7×7 pixels, but not limited thereto.

The parameter selector 25 searches the data table stored in the parameter storage 24 to read out a noise removing parameter (i.e., $\epsilon$ value) suitable for the road surface condition determined by the road surface condition determination unit 23. The read-out noise removing parameter is output to the noise remover 26, which is used as a noise removal unit.

The noise remover 26 conducts a noise removing processing by employing a noise removing method using the $\epsilon$ filter. Specifically, by using the noise removing parameter (i.e., $\epsilon$ value) output from the parameter selector 25, the noise removing processing is conducted for light intensity data of surrounding pixels surrounding a target pixel.

Figure 8:
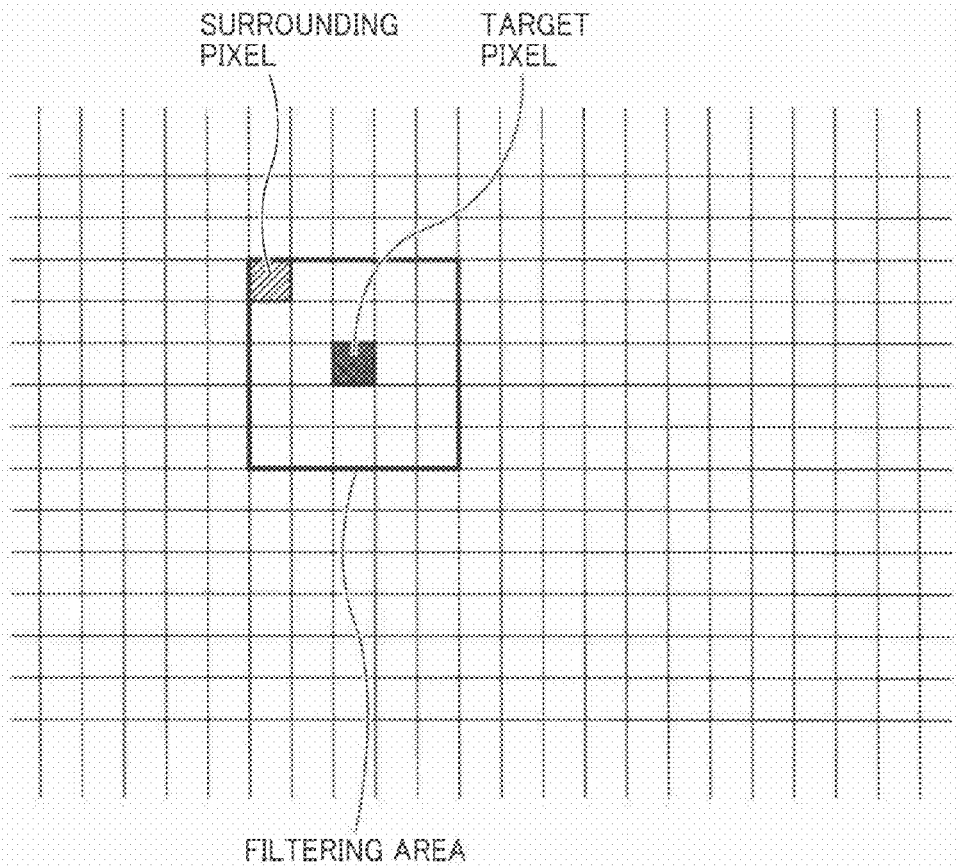
FIG. 8 shows a filtering area for a noise removing method using a ϵ filter.

Hereinafter, a noise removing method using a $\epsilon$ filter having 5×5 pixels is explained as one example with reference to FIG. 8. The window such as 5×5 pixels includes a target pixel at the center of window, and surrounding pixels existing around the target pixel. When the noise removing is conducted for such 5×5 pixels, the absolute difference value of light intensity between the target pixel and the surrounding pixels are compared with a $\epsilon$ value (or threshold value) used as the noise removing parameter.

When the absolute difference value is less than the $\epsilon$ value (or threshold value), the relevant surrounding pixels are used for the averaging process.

When the absolute difference value is greater than the $\epsilon$ value (or threshold value), it is determined that the light intensity data of relevant surrounding pixels are noise component or information, and the light intensity data of such surrounding pixels such are not used for the averaging process. By conducting such noise removing method, surrounding pixels having light intensity value, which is too different from the light intensity value of the target pixel, can be determined and removed as the noise component.

If the ϵ value used as a threshold value is set to a great value, the noise can be removed with a great amount. However, if the ϵ value is set to a high value, an edge component defining a boundary of an identification target object may be removed as noise with a high probability, by which the edge component that needs to be maintained as the captured image after removing the noise may decrease. Therefore, when conducting the noise removing processing, the ϵ value or threshold value needs to be adjusted to a suitable value in view of noise component and edge component.

Further, as for other noise removing methods not using the ϵ filter such as a noise removing method using a bilateral filter, a wavelet conversion, or the like, the determination of noise removing parameter for the noise removing processing is also important. In this disclosure, the "noise removing processing" means an image processing for reducing or removing noise from captured image data, which may include noise. Therefore, in this disclosure, "noise removing" means removing noise from spectroscopic image data completely and reducing noise from spectroscopic image data.

The noise remover 26 removes noise from the P-polarized light intensity data and S-polarized light intensity data, and then transmits the P-polarized light intensity data and S-polarized light intensity data to a monochrome image processor 13. The monochrome image processor 13 computes monochrome image intensity (or monochrome light intensity) for each pixel, which is a total of polarized light intensity of each pixel (i.e., P-polarized light intensity+S-polarized light intensity). The monochrome image processor 13 may process image data as similar to the monochrome image processor 21, but the monochrome image processor 13 processes the polarized image data after removing the noise.

Based on the monochrome image intensity data (or monochrome light intensity data) computed by the monochrome image processor 13, a monochrome image can be generated. The monochrome image intensity data computed by the monochrome image processor 13 is output to the white line identification unit 14, useable as a line detector.

The noise remover 26 removes noise from the P-polarized light intensity data and S-polarized light intensity data, and then transmits the P-polarized light intensity data and S-polarized light intensity data to a polarization intensity difference image processor 15. Then, the polarization intensity difference image processor 15 computes a polarization intensity difference for each pixel as an identification index value using the P-polarized light intensity data and S-polarized light intensity data which are removed noise by the noise remover 26.

The polarization intensity difference image processor 15 may process image data as similar to the polarization intensity difference image processor 22, but the polarization intensity difference image processor 15 processes the polarized image data after removing the noise.

Based on the polarization intensity difference computed by the polarization intensity difference image processor 15, a polarization-intensity-difference-based image data can be generated. The polarization-intensity-difference-based image data computed by the polarization intensity difference image processor 15 is output to an object identification unit 18.

Based on the monochrome image intensity data (or monochrome light intensity data) computed by the monochrome image processor 13 after removing the noise, the white line identification unit 14 identifies a white line on a road surface by conducting a following process. The white line may mean any lines to define an area on a road such as solid lines, dotted lines, broken lines, double lines, which may be painted with any color such as yellow.

Typically, as for normal roads which may be made of asphalt or the like having black color, lane markings (used as defining line) may be painted with white color having a high contrast with respect to the asphalt having black color so that drivers can easily recognize the lane markings. Therefore, the intensity of lane marking such as white line is greater than the intensity of other objects such as asphalt. Therefore, when the monochrome image intensity data (or monochrome light intensity data) exceeds a given threshold value, such monochrome image intensity data can be determined as a white line.

Further, in an example embodiment, the monochrome image intensity data (or monochrome light intensity data) is a total value of P-polarized light intensity and S-polarized light intensity obtained by the polarized light camera 10.

The identification result of white line edge portion identified by the white line identification unit 14 can be used for various processes. For example, a monochrome image generated by using light intensity data computed by the monochrome image processor 13 can be displayed on a display device using a cathode ray tube (CRT) or a liquid crystal display (LCD) used as an information presenting (or reporting) unit and mounted inside a vehicle, in which a front view image may be displayed. Further, the information of white line in the captured image can be processed so that the white line can be displayed on the display device as useful information for a driver that the driver can easily view the information.

With such a configuration, even if the driver is hard to recognize the white line by his/her eyes, the driver can recognize a relative positional relationship between the vehicle and the white line by viewing a front view image of the vehicle using the display device, by which it becomes easy to drive the vehicle within the traffic lane defined by the white line.

Further, for example, based on the positional information of white line identified by the white line identification unit 14, a relative positional relationship between the vehicle and white line can be determined using a given process. Specifically, it can be determined whether his vehicle is running deviated from a traffic lane defined by the white line. If it is determined that his vehicle is running deviated from the traffic lane, an alarm sound or the like may be generated. Further, if it is determined that the vehicle is running deviated from the traffic lane, an automatic braking system can be activated to decrease a driving speed of the vehicle.

When the white line identification unit 14 identifies the white line edge portion, information to identify a position of white line edge portion in a captured image is output to the object identification unit 18. Then, the white line can be removed from the monochrome image processed by the monochrome image processor 13, and the monochrome image data without the white line can be prepared and output to an image selection unit.

In contrast, when the white line identification unit 14 cannot identify the white line edge portion, information to identify a position of white line edge portion in a captured image is not output to the object identification unit 18.

The object identification unit 18 can identify a road side-end edge portion using a polarization intensity difference of polarization-intensity-difference-based image. Then, the object identification unit 18 compares the identification result of the road side-end edge portion and shape template stored in a shape storage 17 to identify an image area or position at a road side-end using a method to be described later.

In an example embodiment, the identification target object may be road side-end obstacles such as side walls, guardrails/crash barriers, stepped portion disposed near the road side-end of the road surface, and a road side-end edge portion, which is a boundary between the road surface and road side-end. But the identification target object is not limited thereto. For example, telegraph poles/utility poles, streetlamps/streetlights, traffic markings, automobiles on the road surface, persons, animals, and bicycles on the road surface or the shoulder of a road can be used as identification target objects. Such objects may be identified to evade collisions.

Further, in an example embodiment, if the white line identification unit 14 cannot recognize white line edge portions, the white line edge portions may be identified as an identification target object. As similar to white line identified by the white line identification unit 14, the identification result of the identified road side-end edge portion can be used for various processing for the operator support system.

For example, a monochrome image generated using light intensity data computed by the monochrome image processor 13 can be displayed on a display device using a cathode ray tube (CRT) or a liquid crystal display (LCD), used as an information presenting or reporting unit and mounted inside a vehicle, in which a front view image may be displayed. The positional information of road side-end edge portion in the captured image can be processed and displayed on the display device as useful information for drivers, which is easy to view for the drivers.

With such a configuration, even if the driver is hard to recognize the road side-end by his/her eyes, the driver can recognize a relative positional relationship between the vehicle and the road side-end by viewing the front view image of the vehicle using the display device, by which it becomes easy to recognize the relative positional relationship between the vehicle and the road side-end, and thereby a collision with road side-end obstacles can be evaded and safety driving can be conducted easily.

Further, for example, based on the positional information of road side-end edge portion identified by the object identification unit 18, a relative positional relationship between the vehicle and road side-end edge portion can be determined using a given process. Specifically, it is determined whether the vehicle is running close to the road side-end. If it is determined that the vehicle is running close to the road side-end, an alarm sound or the like may be generated. Further, if it is determined that the vehicle is running close to the road side-end, an automatic braking system can be activated to decrease a driving speed of the vehicle.

The shape storage 17, used as shape information storage, stores various data as shape template, which is used as shape information by the object identification unit 18. The shape template stored in the shape storage 17 may include shape information of identification target object to be captured by the polarized light camera 10 and identified by the object identification unit 18. The identification target object includes, for example, a road side-end edge portion to be captured by the polarized light camera 10 and identified by the object identification unit 18. As such, the shape template may include shape information of identification target objects to be included in a captured image.

Therefore, the shape template may include shape information of objects, which may extend along a traffic lane in a substantially parallel manner. Further, the shape template may include size information of objects.

The shape template can be selected in view of shapes of identification target objects. For example, a shape template for a manhole cover, a shape template for non-retroreflective raised pavement marker or retroreflective raised pavement marker defining line, a shape template for metal connection parts used for highways and bridges, a shape template for automobiles, a shape template for telegraph poles/utility poles and streetlamps/streetlights, or the like can be used as the shape template.

Figure 9:
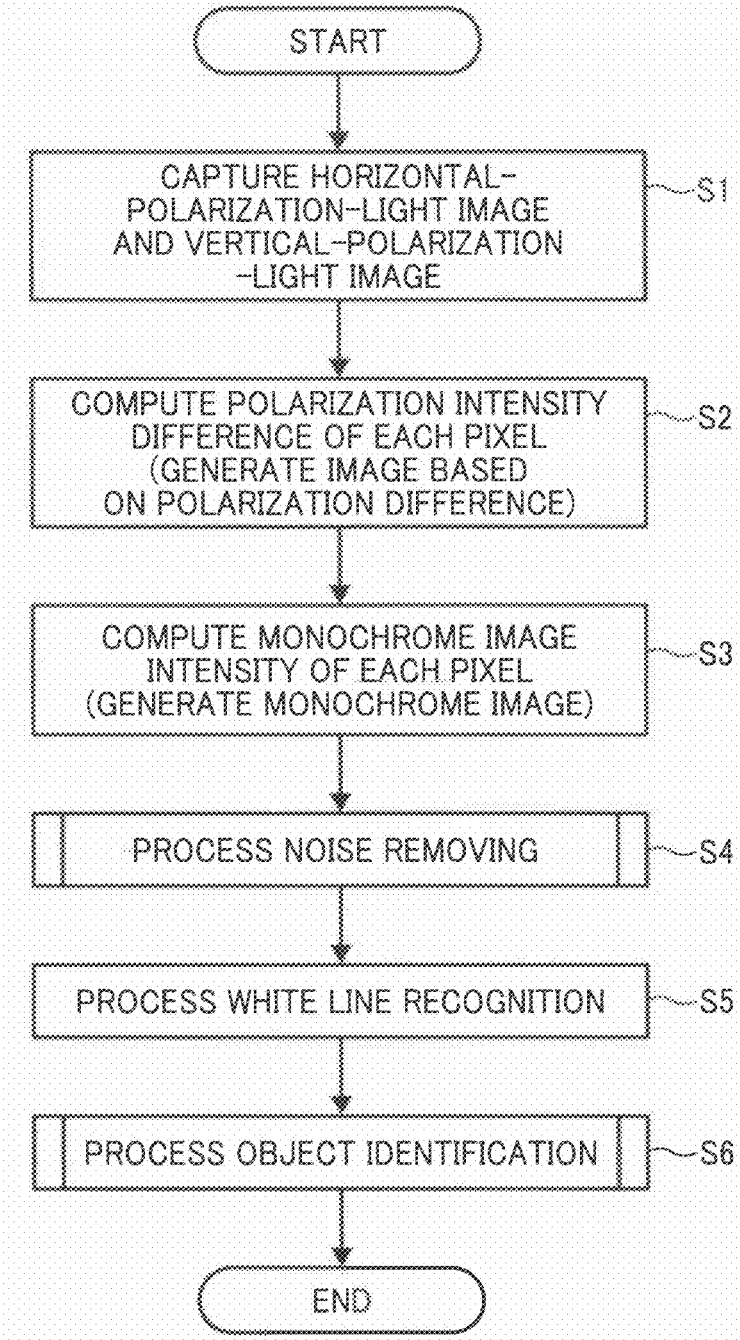
FIG. 9 shows a flowchart of steps of process of identifying a road side-end edge portion and a white line edge portion.

A description is given of process of identifying an identification target object such as a road side-end edge portion and a white line edge portion using the operator support system according to an example embodiment with reference to FIG. 9. FIG. 9 shows a flowchart of steps of process of identifying a road side-end edge portion and a white line edge portion.

When RAW image data of polarized light is captured by the polarized light camera 10, horizontal-polarization image data, obtained from P-polarized light intensity data included in the RAW image data of polarized light, is stored in the horizontal-polarization image memory 11, and vertical-polarization image data, obtained from S-polarized light intensity data included in the RAW image data of polarized light, is stored in the vertical-polarization image memory 12 (step S1).

The polarization intensity difference image processor 22 computes polarization intensity difference (or polarization difference level) for each pixel as the identification index value using the calculation formula (1), P-polarized light intensity data stored in the horizontal-polarization image memory 11 and S-polarized light intensity data stored in the vertical-polarization image memory 12 (step S2). The polarization-intensity-difference-based image data, obtained by such computation, is stored in an image memory of the polarization intensity difference image processor 22.

Further, the monochrome image processor 21 computes image intensity (or monochrome light intensity), which is a total of P-polarized light intensity and S-polarized light intensity of one pixel, for each pixel using P-polarized light intensity data stored in the horizontal-polarization image memory 11 and S-polarized light intensity data stored in the vertical-polarization image memory 12 (step S3). The monochrome image data obtained by such computation is stored in an image memory of the monochrome image processor 21, and a noise removing processing is conducted using a suitable noise removing parameter (step S4).

Figure 10:
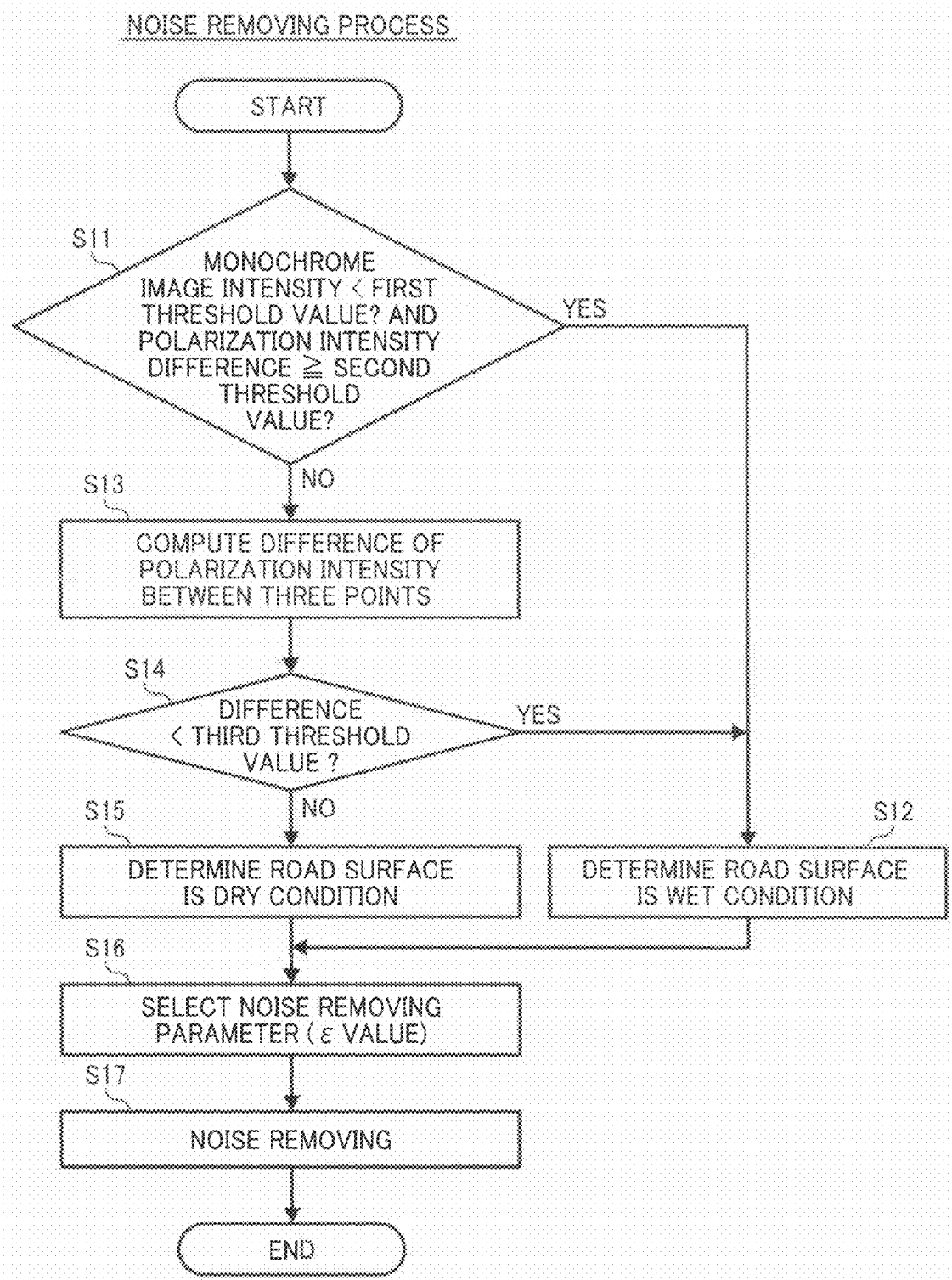
FIG. 10 shows a flowchart of steps of a noise removing processing.

FIG. 10 shows a flowchart of the noise removing processing at step S4 of FIG. 9. The road surface condition determination unit 23 determines a road surface condition in an image capturing area using monochrome image intensity data computed by the monochrome image processor 21, and polarization intensity difference data computed by the polarization intensity difference image processor 15.

A description is given of a case that determines whether a road surface is at a dry condition or a wet condition, and conducts the noise removing processing using a noise removing parameter (i.e., ϵ value) matched to each of conditions.

The road surface condition determination unit 23 determines whether monochrome image intensity data computed by the monochrome image processor 21 is less than a first threshold value, and also determines whether polarization intensity difference data computed by the polarization intensity difference image processor 15 is a second threshold value or more set in advance (step S11). Such first and second threshold values can be set as preset values.

If it is determined that the monochrome image intensity is less than the first threshold value and the polarization intensity difference data is the second threshold value or more (step S11: Yes), the road surface condition determination unit 23 determines that the road surface is at the wet condition (step S12).

If it is determined that the monochrome image intensity is the first threshold value or more, or if it is determined that the polarization intensity difference data is less than the second threshold value (step S11: No), the road surface condition determination unit 23 computes difference value of polarized light intensity between three points disposed on a same line (see FIG. 11). The three points are point A (left side of captured image), point B (center of captured image), and point C (right side of captured image) as shown in FIG. 11. Specifically, the road surface condition determination unit 23 computes a difference value of polarization intensity between the points A and B, and a difference value of polarization intensity between the points B and C (step S13). Then, it is determined whether the both of two difference values are less than a third threshold value (step S14).

If it is determined that the two difference values are less than the third threshold value (step S14: Yes), the road surface condition determination unit 23 determines that the road surface is at the wet condition (step S12). On one hand, if it is determined that at least one of the two difference values is the third threshold value or more (step S14: No), the road surface condition determination unit 23 determines that the road surface is at the dry condition (step S15).

FIG. 12(*a*) shows an expanded schematic view of a road surface at the wet condition, and FIG. 12(*b*) shows an expanded schematic view of a road surface at the dry condition. When the road surface is at the wet condition, the road surface is covered by water, and a reflecting light reflecting from the wet-conditioned road surface passes the water and then air, and is received by the polarized light camera 10. The passing ratio of P-polarized light component from water to air is greater than the passing ratio of S-polarized light component from water to air. Therefore, if the P-polarized light component is greater the S-polarized light component, it can be determined that the road surface is at the wet condition (FIG. 12(*a*)). If the P-polarized light component and S-polarized light component are substantially same, it can be determined that the road surface is at the dry condition (FIG. 12(*b*)). As such, by comparing light intensity value and polarization intensity difference with the threshold values set in advance such as the first and second threshold values, the road surface condition can be determined.

By using such feature, if it is determined that the monochrome image intensity is less than the first threshold value, and the polarization intensity difference is the second threshold value or more at step S11, it can be determined that the road surface is at the wet condition (step S12).

Figure 13:
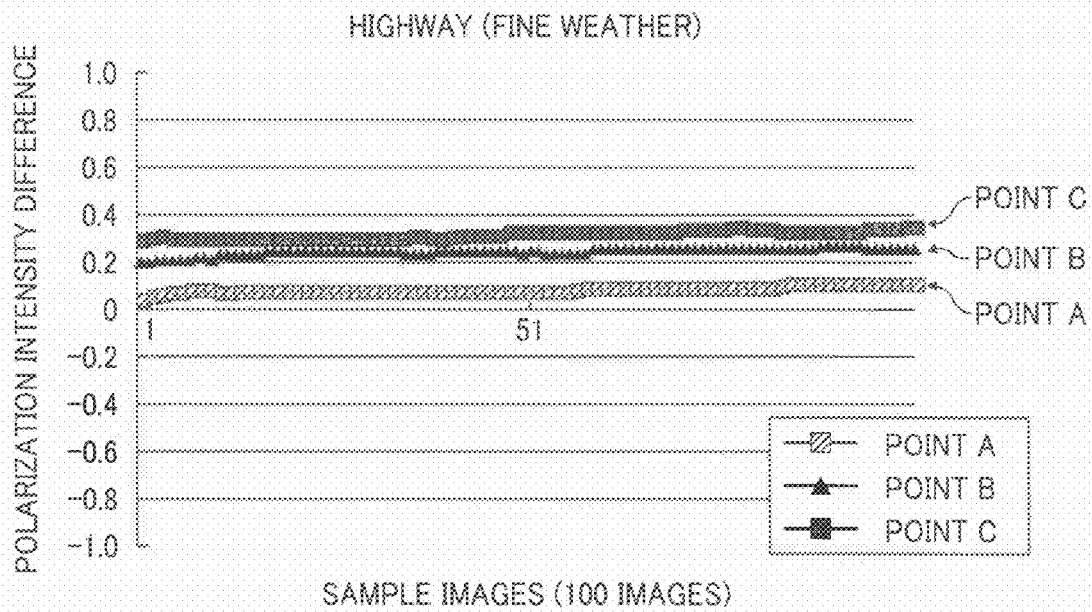
FIG. 13 shows a graph plotting polarization intensity difference at three points shown in FIG. 11 when the road surface is dry condition, and the weather is fine.
Figure 14:
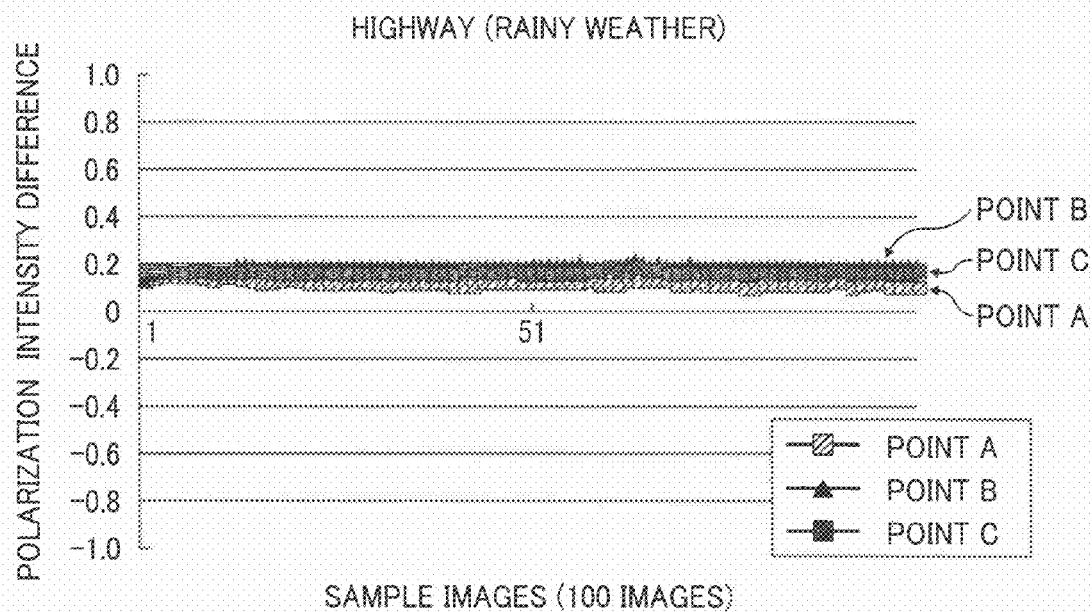
FIG. 14 shows a graph plotting polarization intensity difference at three points shown in FIG. 11 when the road surface is wet condition, and the weather is rainy.

FIG. 13 shows a graph plotting the polarization intensity difference at the three points such as point A, point B, and point C shown in FIG. 11, wherein the weather was fine weather and the road surface of highway was at the dry condition and 100 sample images were taken. FIG. 14 shows a graph plotting polarization intensity difference at the three points such as point A, point B, and point C shown in FIG. 11, wherein the weather was rainy weather, and the road surface of highway was at the wet condition and 100 sample images were taken.

As shown in such graphs, the fluctuation of polarization intensity difference between the three points for the wet condition is smaller than the fluctuation of polarization intensity difference between the three points for the dry condition. By using such feature, it can be determined whether the road surface is at the dry condition or wet condition. By using such feature at steps S13 S14 (see FIG. 10), the difference value of a polarization intensity between the points A and B and the difference value of polarization intensity between the points B and C are computed, and if both of the polarization intensity difference values are less than the third threshold value, it can be determined that the road surface is at the wet condition.

When the road surface condition is determined as such, the parameter selector 25 selects and reads a noise removing parameter (e.g., $\epsilon$ value), matched to the determination result of the road surface condition, from a data table in the parameter storage 24 (step S16).

The noise remover 26 conducts a noise removing processing using the above described noise removing method using the $\epsilon$ filter by using P-polarized light intensity data stored in the horizontal-polarization image memory 11, S-polarized light intensity data stored in the vertical-polarization image memory 12, and the $\epsilon$ value selected by the parameter selector 25 (step S17).

A description is given of evaluation result of the noise removing processing using the $\epsilon$ filter, in which the $\epsilon$ value for the dry condition was set from 45 to 55, and the $\epsilon$ value for the wet condition was set from 60 to 70, and 100 sample images were taken for the dry and wet conditions.

The evaluation functions are standard deviation rate (SDR) indicating a noise reduction rate (calculation formula (3)) and the edge slope rate (ESR) indicating an edge maintained rate (calculation formula (4)).

$SD_{original}$ is a standard deviation of light intensity data for 40×40 pixels on an original image before applying the $\epsilon$ filter. $SD_{filtered}$ is a standard deviation of light intensity data for 40×40 pixels on an original image after applying the $\epsilon$ filter. The greater the SDR value, the greater the noise reduction.

$ES_{original}$ is an edge slope on an original image before applying the $\epsilon$ filter. $ES_{filtered}$ is an edge slope on an original image after applying the $\epsilon$ filter. The greater the ESR value, the greater the edge is maintained after the noise removing processing.

$$SDR(\%) = (SD_{original} - SD_{filtered})/SD_{original} \times 100 \quad (3)$$

$$ESR(\%) = ES_{filtered}/ES_{original} \times 100 \quad (4)$$

The evaluation was conducted by applying the above mentioned $\epsilon$ value to each of the road surface conditions in the captured images, and the following evaluation results were obtained.

SDR for dry condition=74.55%
ESR for dry condition=86.38%
SDR for wet condition=76.45%
ESR for wet condition=88.67%

When the noise removing processing completes as such, the monochrome image processor 13 computes monochrome image data using the P-polarized light intensity data and S-polarized light intensity data having removed the noise, and then the white line identification unit 14 conducts a white line identification processing at step S5 of FIG. 9 using such monochrome image data and the above described method.

Further, the polarization intensity difference image processor 15 computes the polarization intensity difference image data using the P-polarized light intensity data and S-polarized light intensity data after removing the noise, and then the object identification unit 18 conducts an object identification processing of identification target object using such of polarization intensity difference image data at step S6 of FIG. 9. Hereinafter, the road side-end edge portion is used as the identification target object, but other object such as white line edge portion can be similarly used as the identification target object.

Figure 15:
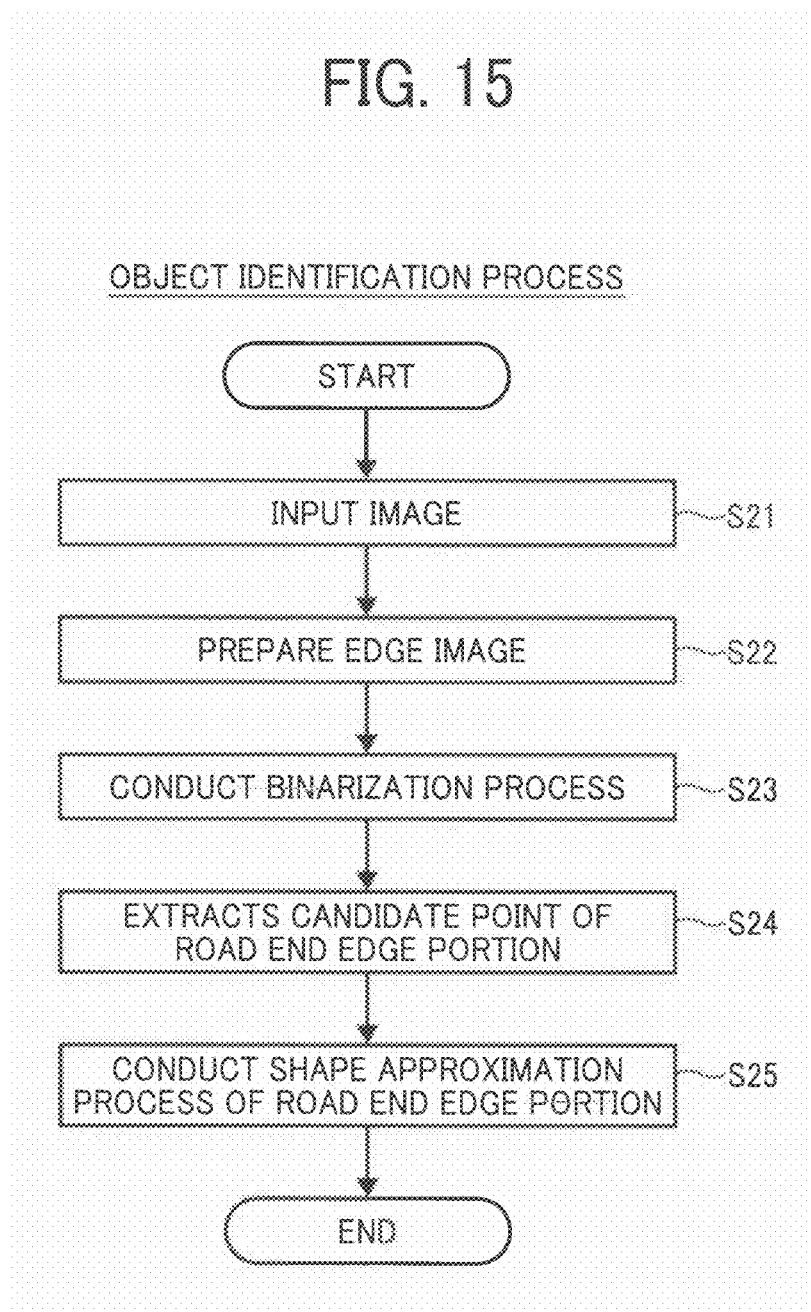
FIG. 15 shows a flowchart of steps of object identification processing.

FIG. 15 shows a flowchart of object identification processing at step S6 of FIG. 9. In the object identification processing, the image having removed the noise component by conducting the above described noise removing processing (e.g., polarization-intensity-difference-based image) is input to conduct an edge determination processing for the image (step S21).

In the edge determination processing, an edge image is prepared based on the image after removing the noise component (e.g., polarization-intensity-difference-based image) (step S22). The edge image can be prepared by conducting a known edge extraction process to the input image (e.g., polarization-intensity-difference-based image) having removed the noise component. By conducting the edge extraction process, an edge value (or edge strength), matched to a changing degree of polarization intensity difference, can be obtained. By expressing the difference of edge value using the difference of polarization intensity, an edge image expressed by the difference of edge value such as the difference of polarization intensity, can be obtained.

Specifically, when the primary differential value, expressing the intensity gradient at a coordinate (x, y), is expressed by vector quantity (fx, fy), wherein "fx" is a differential in X direction, and "fy" is a differential in Y direction, the edge strength can be computed using the following calculation formula (5), in which Roberts operator shown as the following formulas (6) and (7) can be used as differential operators.

$$\sqrt{fx \times fx + fy \times fy} \quad (5)$$

$$f_x = \begin{bmatrix} 0 & 0 & 0 \\ 0 & 1 & 0 \\ 0 & 0 & -1 \end{bmatrix} \quad (6)$$

$$f_y = \begin{bmatrix} 0 & 0 & 0 \\ 0 & 0 & 1 \\ 0 & -1 & 0 \end{bmatrix} \quad (7)$$

After preparing the edge image as such, a binarization process is conducted for the edge image (step S23). The edge threshold value used for the binarization process can be determined from monochrome image intensity and polarization intensity difference of the polarization-intensity-difference-based image, and the noise removing parameter such as $\epsilon$ value.

Further, the intensity of reflecting light reflected from an object becomes different between the upper part and the lower part of captured image. Because the upper part of captured image captures an image of objet existing at a far side and the lower part of captured image captures an image of objet existing at a near side, the intensity of reflecting light from the upper part becomes smaller than the intensity of reflecting light from the lower part. Therefore, the upper part of captured image and the lower part of captured image have different contrast each other. In view of such different contrast, the edge threshold value can be set differently for the upper part and the lower part of captured image.

The object identification unit 18 extracts candidate points of a road side-end edge portion, which is an identification target object, by using the edge image prepared by the binarization process (step S24). In this extraction process, at first, a plurality of processing lines is set for the edge image processed by the binarization process. In an example embodiment, each of the processing lines is a line composed of pixels aligned and extending in one horizontal direction in the edge image processed by the binarization process. The direction of processing line is not required to be a horizontal direction. For example, the direction of processing line can be a vertical direction or slanted direction. Further, each of processing lines can be composed of pixels with a same number of pixels or different numbers of pixels. Further, the processing lines are not required to be set for all pixels in the edge image processed by the binarization process, but can be set for a part of pixels, which may be suitably selected from all pixels in the edge image processed by the binarization process.

Further, instead of setting the processing lines, the extraction process can be conducted by setting processing blocks, wherein the processing block includes at least two pixels or more in the horizontal direction and the vertical direction. In this extraction process, a plurality of processing blocks is set for the edge image processed by the binarization process. For each of processing blocks, the standard deviation, which indicates the fluctuation level of edge image, processed by the binarization process, is computed.

If the computed standard deviation of one processing block is a reference deviation threshold value or more, it can be determined that an edge exists in such one processing block. Further, the processing block can be defined as a rectangular block or other shaped block. The size of processing block is, for example, 10×10 pixels or so, but not limited thereto. Further, the size of each processing blocks can be set to a same size or different sizes. Further, instead of the standard deviation, other statistical values such as variance or mean deviation can be used.

Typically, the road side-end edge portion, which is an identification target object, exists outside of the white line. Therefore, if the white line identification unit 14 can identify two white lines, positioned at both side of one traffic lane, an edge is searched outside the white line position for each of processing lines to simplify the processing. By conducting such searching for all processing lines, the edge portions existing outside each of the white line can be extracted as candidate points of the road side-end edge portion.

Further, if the white line identification unit 14 cannot identify two white lines, an edge portion can be searched along a direction from the center of image toward the left and right sides of image for each of the processing lines. By conducting such searching for all processing lines, the edge portions can be obtained, and the obtained edge portions can be extracted as candidate points of the road side-end edge portion.

Further, if the white line identification unit 14 can identify only one white line, an edge portion can be searched along a direction from the white line toward the left and right sides of image for each of the processing lines. By conducting such searching for all processing lines, the edge portions existing in an image area, except the white line, can be extracted as candidate points of the road side-end edge portion.

After extracting the candidate points of the road side-end edge portion as such, the object identification unit 18 conducts an approximate shape recognition process for the candidate points of the road side-end edge portion to identify the road side-end edge portion (step S25). Specifically, the object identification unit 18 recognizes a shape composed of the candidate points of the road side-end edge portion, and compares the recognized shape with a shape template of road side-end edge portion stored in the shape storage 17. If the shape composed with the candidate points of the road side-end edge portion is matched to the shape of shape template stored in the shape storage 17, the object identification unit 18 identifies such candidate points of the road side-end edge portion as "road side-end edge portion," and stores the position of such candidate points.

Such approximate shape recognition process is conducted for the extracted candidate points of road side-end edge portion by obtaining an approximate curve. The shape can be recognized using the least-squares method, Hough transformation, a model equation, or the like.

Further, when obtaining the approximate curve, the candidate points of road side-end edge portion, positioned at the lower part of captured image, may be set with a high reliability, and a greater weight value can be preferably set to the candidate points at the lower part to approximate a shape. With such a configuration, even if the candidate points of road side-end edge portion positioned at the upper part of captured image have a low reliability, and the candidate points at the upper part of captured image are misidentified, the road side-end edge portion can be identified correctly using correctly recognized candidate points of road side-end edge portion positioned at the lower part of captured image having a high reliability.

Further, to enhance the identification precision of road side-end edge portion, a following process can be added. Specifically, the above described object identification processing (steps S21 to S25) may be conducted continuously for the polarized image data by capturing images using the polarized light camera 10 at a given time interval.

An area identified as the road side-end edge portion is stored in a memory as a processed result. The road side-end edge portion identified by the current process can be checked by using the past processed result stored in the memory (e.g., processed result of polarized image data that was most recently captured). If the road side-end edge portion identified by the current process is matched to the road side-end edge portion in the past processed result, it is determined that the current processed result has a high reliability. Then, such processed result having high reliability can be used to identify the road side-end edge portion. Based on the current vehicle position and driving direction at a given area, the past processed result for the same given area can be searched, and the past processed result can be used for identifying objects or the like for the current identifying process.

Figure 16:
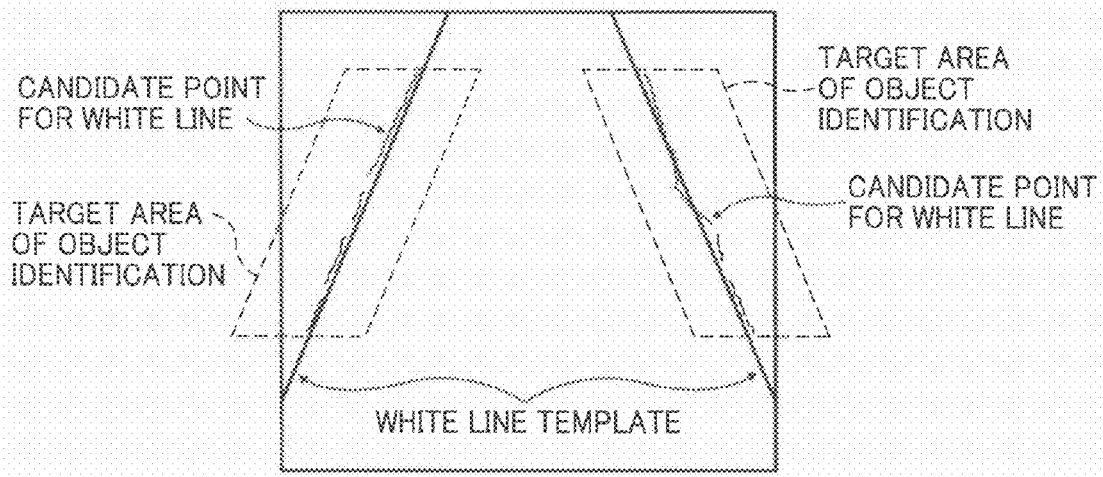
FIG. 16 shows candidate points of a white line indentified from a polarization-intensity-difference-based image and a shape template for white line for a vehicle running on a straight road.
Figure 17:
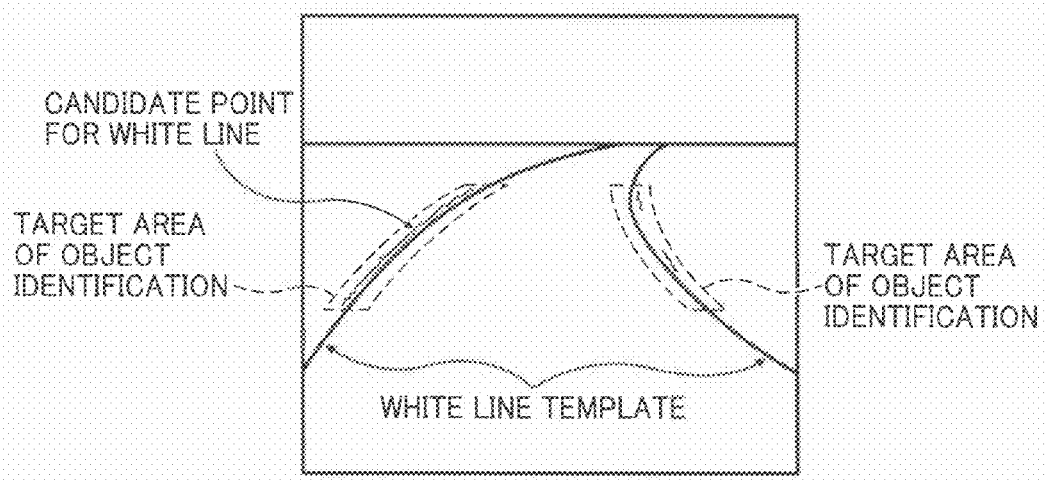
FIG. 17 shows candidate points of a white line indentified from a polarization-intensity-difference-based image and a shape template for white line curving to the right direction for a vehicle running on a road curving to the right curving direction.

A description is given of cases that the white line identification unit 14 cannot identify the white line and the object identification unit 18 conducts an object identification processing to identify the white line using a shape template with reference to FIGS. 16 and 17.

FIG. 16 shows candidate points of the white line indentified from the polarization-intensity-difference-based image and a shape template for white line useable for vehicle moving on a straight road. As similar to the above case for indentifying the road side-end edge portion, candidate points for the white line are extracted from polarization-intensity-difference-based image prepared by the polarization intensity difference image processor 15, and the candidate points for the white line receives the approximate shape recognition process and are compared with the white line template.

A target area of object identification, which receives the object identification processing by the object identification unit 18 may not necessary an entire area of the captured image, but may be a part of the captured image in view of shortening the time required for processing. For example, as shown in FIG. 16, the upper area and lower area of image can be excluded from the target area of object identification. Further, as for the identification of the white line, the center area of image can be excluded from the target area of object identification.

When a shape composed of the candidate points for the white line in the target area of object identification and the shape stored in the white line template can be matched each other, the candidate points can be identified as the white line, and then the position of the candidate points are stored.

As for the area outside the target area of object identification, which has no candidate points for the white line, the white line can be indentified in such outside area of the target area of object identification by extrapolating a white line (or extending the white line) stored in the white line template, and the extended position of the white line in such outside area can be stored. With such a configuration, even if the target area of object identification is a part of the captured image, the white line can be identified for the entire area of the captured image.

FIG. 17 shows candidate points of the white line indentified from the polarization-intensity-difference-based image and a shape template for white line curving to the right direction, which is useable for a vehicle moving on a road curving to the right direction. In a case of FIG. 17, the candidate points for the white line at the left side matches the white line template, but the candidate points for the white line at the right side may not match the white line template.

Because the candidate points for the white line at the left side matches the white line template, the candidate points at the left side can be identified as the white line, and the position of the candidate points at the left side is stored in a memory. In contrast, the candidate points for the white line at the right side do not match the white line template. In such a case, it can be determined that the candidate points are not the white line. However, the position that the white line template is superimposed at the right side can be identified as the white line, and the position of the identified as the white line can be stored in a memory.

As for the object identification device according to an example embodiment, the polarized light camera 10, usable as the image capturing device, receives light reflecting from an object existing in an image capturing area. Specifically, the polarized light camera 10 captures images of two polarized lights having different polarization directions such as P-polarized light component and S-polarized light component, as polarized image of P-polarization image and S-polarization image.

The noise remover 26, useable as the noise removal unit, conducts the noise removing processing to remove noise components included in P-polarization image and S-polarization image captured by the polarized light camera 10 using the noise removing parameter such as $\epsilon$ value.

The monochrome image processor 13 and the polarization intensity difference image processor 15 can be used to divide two polarized images captured by the polarized light camera 10 into each of identification processing areas corresponding to each pixel. Then, as for each pixel, the monochrome image processor 13 and the polarization intensity difference image processor 15 compute an object identification index value such as monochrome image intensity and polarization intensity difference using light intensity data of P-polarization image and S-polarization image having removed the noise component by the noise remover 26. As such, the monochrome image processor 13 and the polarization intensity difference image processor 15 can be used as an index value computing unit.

Based on the monochrome image intensity and polarization intensity difference for each pixel computed by the monochrome image processor 13 and the polarization intensity difference image processor 15, the white line identification unit 14 and the object identification unit 18 determine pixels corresponding to the white line edge portion and road side-end edge portion, and identifies a plurality of pixels corresponding to the white line edge portion and road side-end edge portion as an image area of white line edge portion and road side-end edge portion. As such, the white line identification unit 14 and the object identification unit 18 can be used as an object identification processing unit to conduct the object identification processing.

Further, the monochrome image processor 21 and the polarization intensity difference image processor 22 obtains the monochrome image intensity and polarization intensity difference as the environment information to be used to determine environmental conditions of an object existing in an image capturing area such as dry condition, wet condition or snowed condition. As such, the monochrome image processor 21 and the polarization intensity difference image processor 22 can be used as an environment information obtaining unit.

Based on the obtained environment information such as monochrome image intensity and polarization intensity difference, the road surface condition determination unit 23, usable as an environmental condition determination unit, can determine the environmental conditions such as dry condition, wet condition, or snowed condition for an object existing in an image capturing area.

The parameter storage 24 stores noise removing parameter or $\epsilon$ value that can remove noise component, with a high precision, included in the P-polarization image and S-polarization image captured under a plurality of environmental conditions (dry condition, wet condition, snowed condition). The parameter selector 25 reads out a noise removing parameter or $\epsilon$ value matched to the road surface condition determined by the road surface condition determination unit 23 from the parameter storage 24, and the noise remover 26 conducts the noise removing processing using the noise removing parameter or $\epsilon$ value.

With such a configuration, the noise component can be effectively removed for various road surface conditions such as dry condition, and wet condition, by which the object identification can be conducted with a high precision using the image captured under various road surface conditions.

The noise removing parameter is $\epsilon$ value, which is the threshold value to determine whether the light intensity data of P-polarization image and S-polarization image is a noise component. In the noise removing processing, based on the $\epsilon$ value, it is determined whether the light intensity data of P-polarization image and S-polarization image captured by the polarized light camera 10 is a noise component. Then, an impulse noise removing processing is conducted to remove the light intensity data determined as the noise component so that such noise data is not used for computing the monochrome image intensity by the monochrome image processor 13 and not used for computing polarization intensity difference by the polarization intensity difference image processor 15. With such a configuration, the impulse noise can be effectively removed from images captured under various road surface conditions such as dry condition, wet condition, or the like.

As for the impulse noise removing processing, when the light intensity difference for P-polarization image and S-polarization image between the target pixel and surrounding pixels surrounding the target pixel exceeds the $\epsilon$ value, the light intensity data of concerned surrounding pixels is determined as a noise component and removed. With such a configuration, the impulse noise can be effectively removed with a simple process.

As for the noise removing processing, after conducting the impulse noise removing processing, based on the light intensity data for P-polarization image and S-polarization image of the target pixel and surrounding pixels surrounding the target pixel, a noise removing processing may be conducted to remove a high frequency noise included in light intensity data in the noise removing processing area defined by the target pixel and the plurality of surrounding pixels. With such a configuration, the high frequency noise can be effectively removed from images captured under various road surface conditions such as dry condition, wet condition, or the like.

The noise removing parameter or $\epsilon$ value, set for each of the road surface conditions and stored in the parameter storage 24, can be obtained as follows. A plurality of sample images of polarized image, for example, 100 sample images, are taken, in which the P-polarization image and S-polarization image are captured for a plurality of image capturing areas under each of various environmental conditions. The noise removing parameter or $\epsilon$ value is adjusted to remove noise components included such P-polarization image and S-polarization image captured under each environmental condition with a high precision. With such a configuration, the noise removing parameter or $\epsilon$ value can be effectively adjusted to various road surface conditions.

As for the object identification index value, a polarization light ratio shown by the calculation formula (2) can be used to indicate a ratio of light intensity between P-polarization image and S-polarization image captured by the polarized light camera 10.

As for the object identification index value, the polarization intensity difference, which is a ratio of a difference of P-polarized light intensity and S-polarized light intensity and a total of P-polarized light intensity and S-polarized light intensity for each pixel can be used. When the monochrome image intensity is used as the object identification index value but the object identification precision using the monochrome image intensity is not so high, the object identification can be effectively conducted with a high precision using any one of polarized light ratio and polarization intensity difference as the object identification index value.

As for the environment information, the object identification index value such as monochrome image intensity or polarization intensity difference can be employed to determine the road surface condition. With such a configuration, the environmental condition information can be obtained without a special device to obtain environment information, by which the whole system can be simplified.

The road surface condition can be determined using a variation of polarization intensity difference between a plurality of points such as points A, B, and C in an image capturing area. With such a configuration, the road surface condition such as dry condition or wet condition can be determined with a high precision.

The object identification device can be applied to a moving object controlling apparatus for a vehicle such as automobile, which is a moving object. For example, a driving support electronic control unit (ECU), used as a movement control unit of vehicle, can use an identification result of the object identification device to activate an automatic braking system.

The object identification device can be applied to an information presenting apparatus of a vehicle such as automobile, which is a moving object, wherein the information presenting apparatus can report useful information to a driver of the vehicle. Such useful information can be generated using the identification result of the object identification device.

Further, in the above described example embodiment, the operator support system is mounted in one vehicle, but it is not required to install all of the operator support system in one vehicle. For example, the vehicle is mounted with only the polarized light camera 10, and the rest of the operator support system can be disposed remotely from the vehicle, in which a person other than the driver may monitor the driving condition of vehicle using the operator support system.

Further, in the above described example embodiment, the road surface condition is used as an environmental condition when identifying an object in an image capturing area. However, the above described system can be used with various environmental conditions other than the road surface condition if the environmental condition may affect the identification precision of object, in which a suitable identification method for environmental conditions may be selected depending on the type of environment conditions.

In the above example embodiment, based on the environment information obtained by the environment information obtaining unit, the environmental condition of an object existing in an image capturing area can be determined. Then, a noise removing parameter matched to the determined environmental condition is read out from the parameter storage, and the noise removing processing is conducted using the noise removing parameter. Each of the noise removing parameters stored in parameter storage is matched to each of environmental conditions, by which the noise component included in the captured two polarized images can be removed with a high precision.

In the above example embodiment, even if the environmental condition of an object existing in an image capturing area changes, a noise component can be removed from the captured image effectively.

An object identification device according to an example embodiment can obtain a spectroscopic image to identify objects based on difference of wavelengths of light coming from the objects at a high speed. The precision of object identification process using the spectroscopic image can be enhanced by conducting a noise removing processing using a noise removing parameter suitable for the spectroscopic image.

A description is given of an operator support system to reduce operating burden on operators of vehicles such as automobiles using an identification result based on a spectroscopic image, but the application of this invention is not limited thereto. In the following example, the difference of light wavelength from a moving object such as a tail lamp of in-front automobile or a head lamp of incoming automobile, and light wavelength of road side-end objects such as automatic vending machine (ATM) and streetlamps/streetlights can be detected to differentiate and identify these objects.

Figure 18:
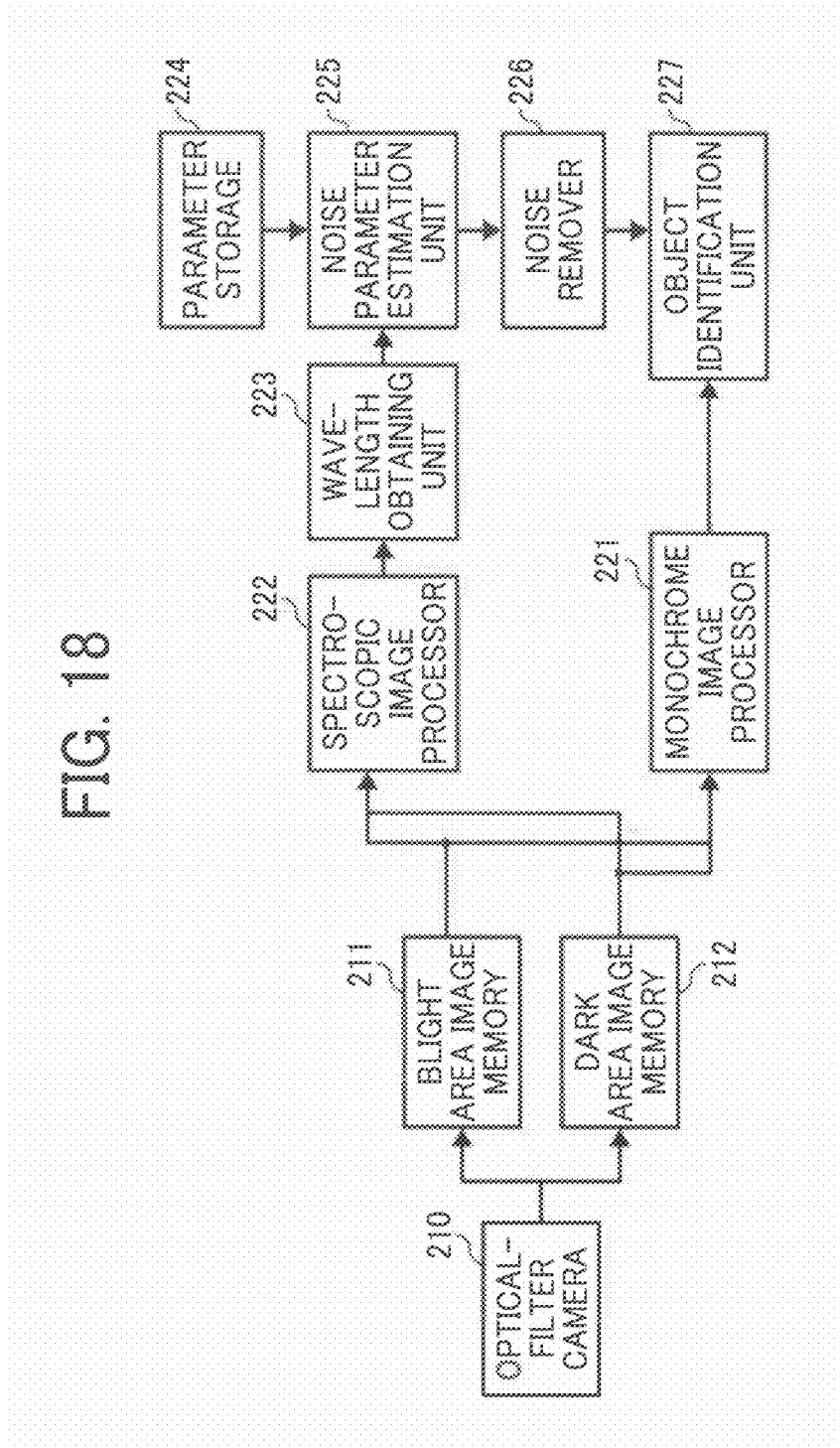
FIG. 18 shows another functional block diagram of operator support system according to another example embodiment.

FIG. 18 shows a functional block diagram of an operator support system according to an example embodiment. An optical filter camera 210, which is an image capturing device, is mounted in an automobile, and the optical filter camera 210 captures scenes around the automobile, for example, when the automobile (or moving object) is running on a road. The optical filter camera 210 captures scenes on or above a road surface when the automobile is running, in which RAW image data is obtained for each of pixels (or processing areas) as light intensity data. As described later, the optical filter camera 210 includes an image sensor having a plurality of pixels, in which two adjacent pixels, which are next to each other, are used to capture a bright image and a dark image (one pixel for bright image, and the other pixel for dark image).

Therefore, when the image data (or RAW image data) is captured by the optical filter camera 210, the two adjacent pixels capture a bright image and a dark image, and thereby the image sensor of the optical filter camera 210 captures a two-dimensional image which includes bright and dark areas two-dimensionally and repeatedly with a given interval (i.e. bright and dark areas appear periodically).

The data of pixel, corresponding to the bright image data (or bright light intensity data) of RAW image data having a given light intensity, is stored in a bright area image memory 211, and the data of pixel, corresponding to the dark image data (or dark light intensity data) of RAW image data is stored in a dark area image memory 212. The bright image data in the entire area of captured image is used as bright image data, and the dark image data in the entire area of captured image is used dark image data. The bright image data and dark image data are both transmitted to a monochrome image processor 221 and a spectroscopic image processor 222. Such processing units and other processing units to be described later may be devised as controllers configured with using various types of processors, circuits, or the like such as a programmed processor, a circuit, an application specific integrated circuit (ASIC), used singly or in combination.

Figure 19:
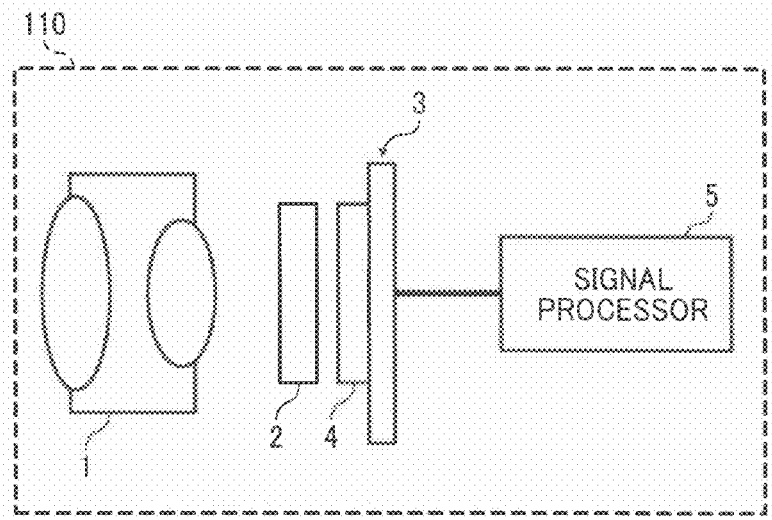
FIG. 19 shows a schematic configuration of optical filter camera useable for the operator support system of FIG. 18.

A description is given of configuration and operation of the optical filter camera 210 with reference to FIG. 19. FIG. 19 shows a schematic configuration of the optical filter camera 210 according to an example embodiment. The optical filter camera 210 includes, for example, an image capture lens 1, an optical filter 2, a sensor base 3, an image sensor 4, and a signal processor 5. The image sensor 4 includes a pixel array having arranged pixels in two-dimensional directions, and the image sensor 4 is disposed on the sensor base 3. The signal processor 5 receives analog signals, output from the sensor base 3, and converts the analog signals to digital signals to prepare image data of captured image, and outputs the digital image data. Light coming from an image capturing area including a photographic subject passes through the image capture lens 1, passes through the optical filter 2, and then converted to an electrical signal corresponding to the light intensity by the image sensor 4.

When the signal processor 5 receives the electrical signal (or analog signal) from the image sensor 4, the signal processor 5 converts the electrical signal (or analog signal) to a digital signal of captured image data, which indicates light intensity at each pixel on the image sensor 4. Then, the signal processor 5 outputs the digital signal of captured image data and a horizontal synchronizing signal and a vertical synchronizing signal of image to the bright area image memory 211 and the dark area image memory 212. The bright image data is stored in the bright area image memory 211, and the dark image data is stored in the dark area image memory 212.

Figure 20:
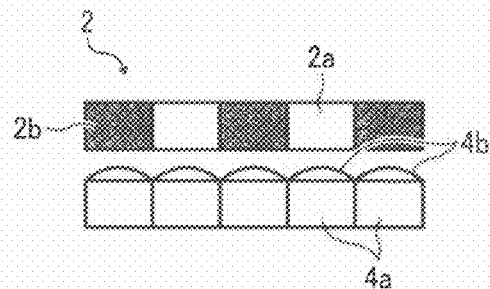
FIG. 20 shows a schematic expanded view of an optical filter and an image sensor of the optical filter camera of FIG. 19.

FIG. 20 shows a schematic expanded view of the optical filter 2 and the image sensor 4. The image sensor 4 is an image sensor such as a charge coupled device (CCD), a complementary metal oxide semiconductor (CMOS), or the like, and employs photodiodes 4a as light receiving elements. The photodiodes 4a are arranged as a two-dimensionally array, and each of the photodiodes 4a is disposed for each pixel. Further, a micro lens 4b is disposed at the incident light side of each of the photodiodes 4a to enhance the light collection efficiency of the photodiodes 4a. The image sensor 4 can be formed on the sensor base 3 by bonding the image sensor 4 on a printed wiring board (PWB) using a wire bonding method or the like. The optical filter 2 is disposed near the micro lens 4b of the image sensor 4.

Figure 21:
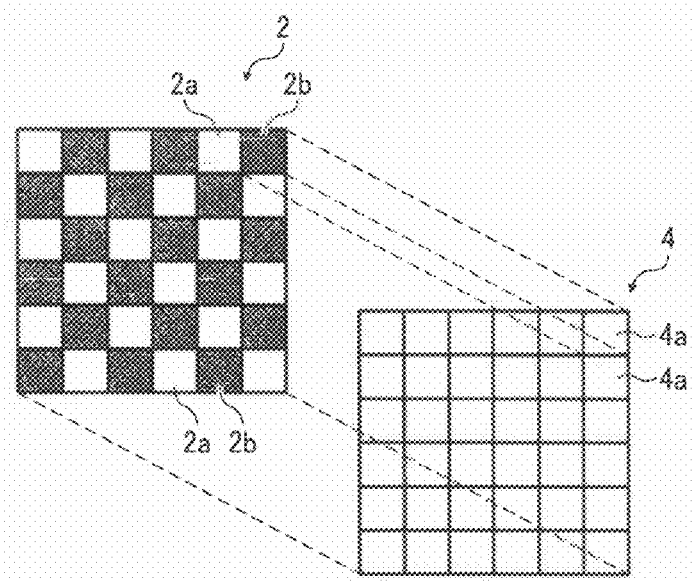
FIG. 21 shows a relation of a grid pattern of optical filter and a pixel pattern of image sensor of FIG. 20.

As shown in FIG. 21, the optical filter 2 includes light passing areas 2a to pass through a light, and light shielding areas 2b to shield a light, which are arranged next to each other alternatively as a two-dimensional grid pattern, by which an area-divided grid pattern, which may be called as a checkerboard pattern is formed. Each one of the light passing areas 2a and each one of the light shielding areas 2b correspond to each pixel (i.e., one photodiode 4a) of the image sensor 4 as shown in FIG. 21.

The light passing through the light passing area 2a diffracts to a back side of the light shielding area 2b. The diffraction phenomenon has a wavelength-dependency, in which the longer the wavelength, the greater the angle of diffraction (the more the light flux spread). In an example embodiment, as described later, a spectroscopic image depending on wavelength can be obtained using a difference of diffraction angle.

The optical filter 2 can be prepared by forming the light passing areas and light shielding areas on a glass plate. To generate preferable diffraction, the interval of the grid pattern is set to, for example, from one wavelength to ten wavelengths or so.

The interval of the grid pattern is set to one pixel size of the image sensor 4 such as a several μm. The interval of the grid pattern and the pixel size of the image sensor 4 may not need to be corresponded 1 to 1 basis. For example, the interval of the grid pattern and the pixel size of the image sensor 4 is set to "1 to M" basis, which means one grid width or one grid area can be corresponded to "M" pixels. Further, the interval of the grid pattern of the optical filter 2 may not need to be a two-dimensional interval structure. For example, the interval of the grid pattern of the optical filter 2 can be one dimensional interval structure.

Further, the grid pattern of the optical filter 2 is not limited to an arrangement of the light passing area 2a and the light shielding area 2b. For example, instead of the light shielding area 2b completely shielding light, a polarization area or polarizer shielding only a given polarization component can be used. Such polarization area or polarizer can pass, for example, P-polarized light component but can shield S-polarized light component.

If such polarization area is formed for the optical filter 2 instead of the light shielding area 2b, the S-polarized light component is shielded at the polarization area, and diffracts at the light passing area 2a. On one hand, the P-polarized light component passes through the entire area of the optical filter 2. Further, the polarization components are not limited two polarization components (e.g., P-polarized light component and S-polarized light component) perpendicular to each other, but other polarization components having different polarization directions each other can be similarly used as the polarization components.

Figure 22:
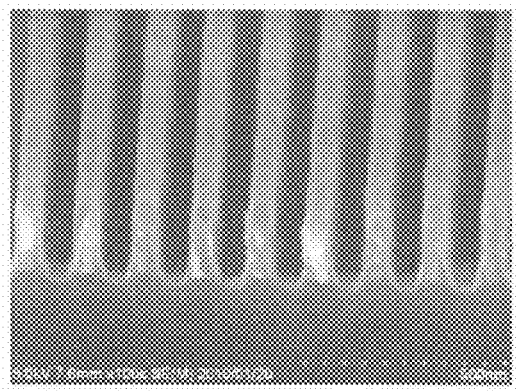
FIG. 22 shows an expanded view of wire grid polarizer useable as a polarization area of optical filter.

Such polarization areas of the optical filter 2 can be formed as a polarizer made of, for example, iodine used for a liquid crystal display, an organic material such as dye material, or as a wire grid polarizer having good durability. As shown in FIG. 22, the wire grid polarizer can be made of a metal such as aluminum, in which conductive material wires are arranged with a given pitch to form a grid pattern.

If the pitch of wire grid polarizer is good enough small compared to the wavelength of incident light (e.g., visible light wavelength: 400 nm to 800 nm) such as one half or less of the wavelength of incident light, the wire grid polarizer can reflect almost all of electric field vector component oscillating in a parallel direction of the conductive material wires, and can pass almost all of electric field vector component oscillating in a perpendicular direction of the conductive material wires, by which the wire grid polarizer can be used to prepare a polarized light oscillating in one direction.

The wire grid polarizer can be manufactured using known semiconductor processes, in which an aluminum thin film is deposited and then the patterning is conducted, and a sub-wavelength concave/convex structure is formed by a metal etching to form a wire grid. Further, the above described grid pattern can be formed by 1) removing some portions from a uniformly formed wire grid layer using an intended grid pattern, or 2) by forming the grid pattern and concave portions of wire grid at one process after depositing aluminum uniformly, wherein the 2) can be conducted with less processing.

When the wire grid polarizer is used, it should be noted that the light diminishing ratio increases when the area of cross section of metal wire increases. Further, when the metal wire has a thickness which is too great compared to a given interval pitch, the passing ratio of light decreases. Further, if the shape of cross section of metal wire, perpendicular to the long direction of metal wire, is a taper shape, the light passing ratio and wavelength dispersibility of polarized light become small in a wide range, by which the light diminishing ratio becomes greater. The metal-wire arranged face is preferably coated with resin or the like to enhance the excoriation resistance and antifouling property.

A description is given of configuration of the optical filter 2 according to an example embodiment with reference to drawings.

(Example 1 of Optical Filter 2)

Figure 23:
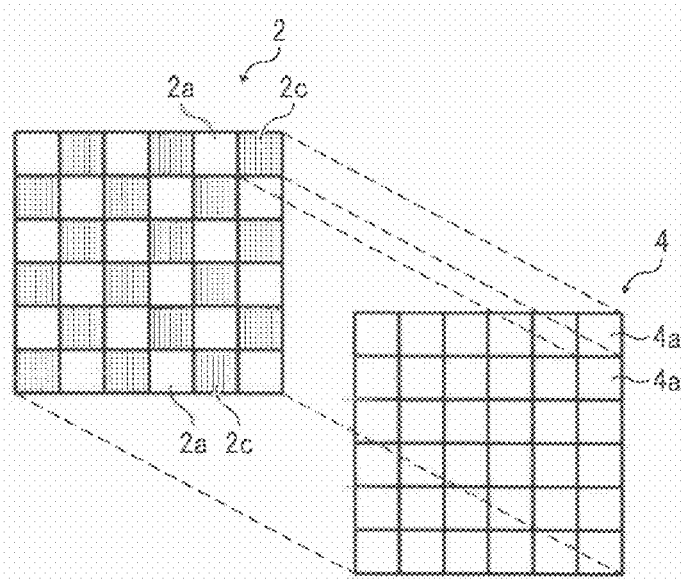
FIG. 23 shows an expanded view of optical filter of example 1.

FIG. 23 shows one example (example 1) of the optical filter 2. The optical filter 2 includes the light passing areas 2a and the polarization areas 2c. Hereinafter, for the simplicity of expression, the term of the light passing area 2a and the polarization area 2c may mean a single area or a plurality of areas. The light passing area 2a can pass both of P-polarized light component and S-polarized light component. The polarization area 2c can pass P-polarized light component but shields S-polarized light component. The light passing area 2a and the polarization area 2c are arranged in a grid pattern, in which the light passing area 2a and the polarization area 2c are alternatively arranged next to each other in two dimensional directions. In other words, the light passing area 2a and the polarization area 2c form a grid pattern, which may be called as a checkerboard pattern, which is an area-divided pattern. The interval of the grid pattern (or one grid width or one grid area) can be matched to a pixel pitch of the image sensor 4.

Figure 24:
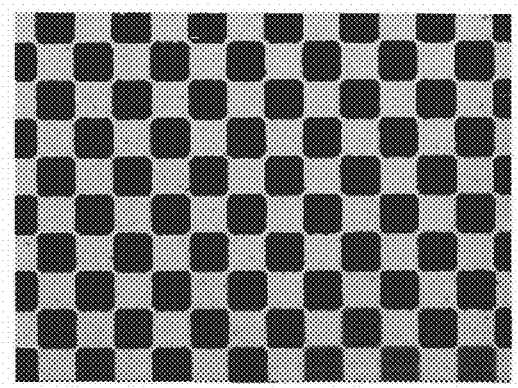
FIG. 24 shows a measurement result image when S-polarized light component entered the optical filter of FIG. 23.

FIG. 24 shows an image of measurement result when the S-polarized light component entered to the optical filter 2 of FIG. 23. The optical filter 2 was prepared by setting one grid size (or one grid width or one grid area) for about 6 μm, and the wire-grid areas and no-wire-grid areas are formed on a glass plate, wherein the wire-grid areas were used as the polarization area 2c, and the no-wire-grid areas were used as the light passing area 2a. The measurement was conducted by attaching a monochrome image intensity camera (or monochrome light intensity camera) on a back face (or light-exiting face) of the optical filter 2. The S-polarized light component was irradiated to the optical filter 2, and the monochrome image intensity camera captured the light that passed the optical filter 2. In FIG. 24, the black area is an area that the light was shielded. As shown in FIG. 24, it can be confirmed that the S-polarized light component is effectively shielded at the polarization area 2c where the wire grid is formed.

(Example 2 of The Optical Filter 2)

Figure 25:
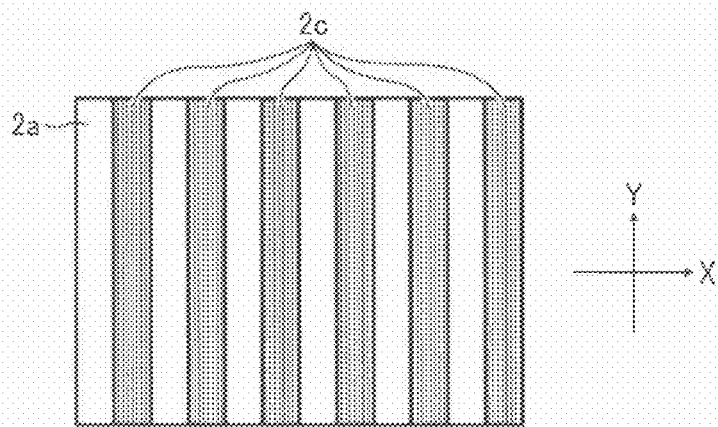
FIG. 25 shows an expanded view of optical filter of example 2.

FIG. 25 shows another example (example 2) of the optical filter 2. The optical filter 2 includes the light passing area 2a and the polarization area 2c. The light passing area 2a can pass both of P-polarized light component and S-polarized light component. The polarization area 2c can pass P-polarized light component but shields S-polarized light component. The light passing area 2a and the polarization area 2c are arranged in a grid pattern, in which the light passing area 2a and the polarization area 2c are alternatively arranged next to each other in one dimensional direction. In other words, the light passing area 2a and the polarization area 2c form a grid pattern, which may be called as a stripe pattern, which is an area-divided pattern. The interval of the grid pattern (or one grid width or one grid area) can be matched to a pixel pitch of the image sensor 4.

When the optical filter 2 is formed with the stripe pattern, which is a grid pattern, as shown in FIG. 24, the positional adjustment with respect to the image sensor 4 may be conducted only in the X direction, and such positional adjustment for the stripe pattern of the optical filter 2 can be conducted easily compared to the positional adjustment for the optical filter 2 having the checkerboard pattern as the grid pattern shown in FIG. 23.

Figure 26:
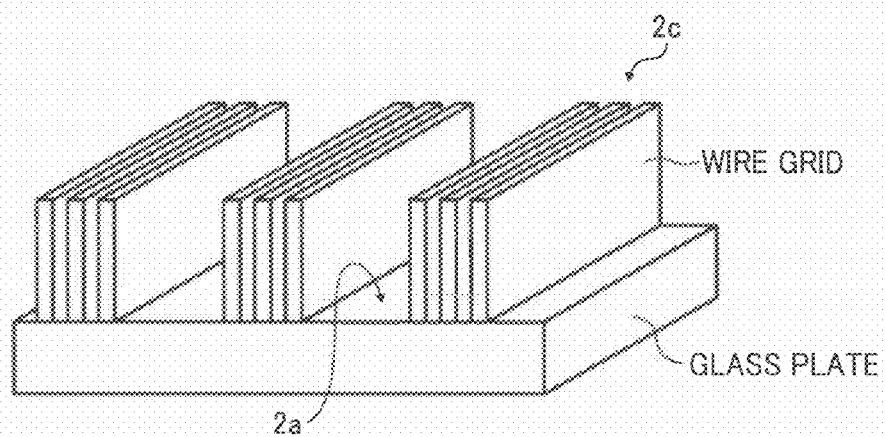
FIG. 26 shows a perspective view of optical filter of FIG. 25.

FIG. 26 shows a perspective view of the optical filter 2 of FIG. 25. The optical filter 2 includes a glass plate and a wire grid pattern formed on the glass plate, in which concave portions and convex portions are disposed with a given interval, and the convex portions include a sub-wavelength wire grid composed of concave/convex structure adapted for a given wavelength.

Figure 27:
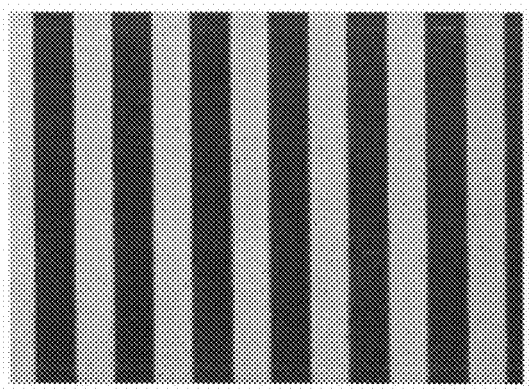
FIG. 27 shows a measurement result image when S-polarized light component entered the optical filter of FIG. 26.

FIG. 27 shows an image of measurement result when the S-polarized light component entered to the optical filter 2 of FIG. 25. The optical filter 2 was prepared by setting one stripe size for about 6 μm, and the wire-grid areas and no-wire-grid areas are formed on a glass plate, wherein the wire-grid areas were used as the polarization area 2c, and the no-wire-grid areas were used as the light passing area 2a. The measurement was conducted by attaching a monochrome image intensity camera on a back face (or light-exiting face) of the optical filter 2. The S-polarized light component was irradiated to the optical filter 2, and the monochrome image intensity camera captured the light that passed the optical filter 2.

In FIG. 27, the black area is an area that the light was shielded. As shown in FIG. 27, it can be confirmed that the S-polarized light component is effectively shielded at the polarization area 2c where the wire grid is formed.

(Example 3 Of Optical Filter 2)

Figure 28:
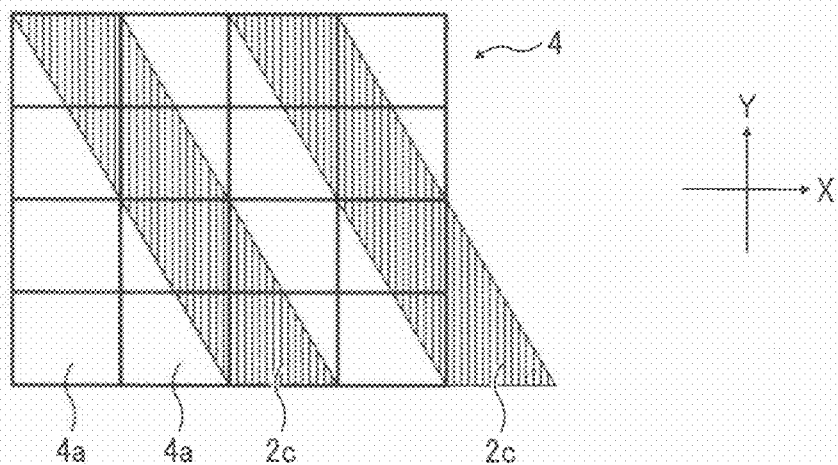
FIG. 28 shows an expanded view of the optical filter of example 3, which a polarized area is overlaid on an image sensor.

FIG. 28 shows another example (example 3) of the optical filter 2. The optical filter 2 includes the light passing area 2a and the polarization area 2c. FIG. 28 shows the polarization area 2c overlaid on the image sensor 4. In the optical filter 2 of FIG. 28, the light passing area 2a and the polarization area 2c are arranged in a grid pattern, in which the light passing area 2a and the polarization area 2c are alternatively arranged next to each other in one dimensional direction. In other words, the light passing area 2a and the polarization area 2c form a grid pattern, which may be called as a stripe pattern, which is an area-divided pattern. Such configuration is similar to the configuration of the optical filter 2 shown in FIG. 25.

As for the optical filter 2 shown in FIG. 25, the long side of the polarization area 2c is set parallel to the pixel line extending in the Y direction. In contrast, as for the optical filter 2 shown in FIG. 28, the long side of the polarization area 2c is not parallel to the pixel line extending in the Y direction and the pixel line extending in the X direction.

As for the optical filter 2 of FIG. 28, a presumed one section of the polarization area 2c has a width of one pixel of the image sensor 4 in the X direction, and a length of two pixels of the image sensor 4 in the Y direction as shown in FIG. 28, and the polarization area 2c exists while slanting with respect to the X and Y directions of the image sensor 4. For example, the presumed one section of the polarization area 2c can be defined with one pixel in the X direction, and two pixels in the Y direction.

By combining such grid pattern having such slanting arrangement pattern and a signal processing method, even if the positioning precision between the pixels of the image sensor 4 and the optical filter 2 cannot be set at a high level when bonding each other, the image light passing the optical filter can be captured using the optical filter 2 as a whole, and such configuration can be devised with a reduced cost.

Figure 29:
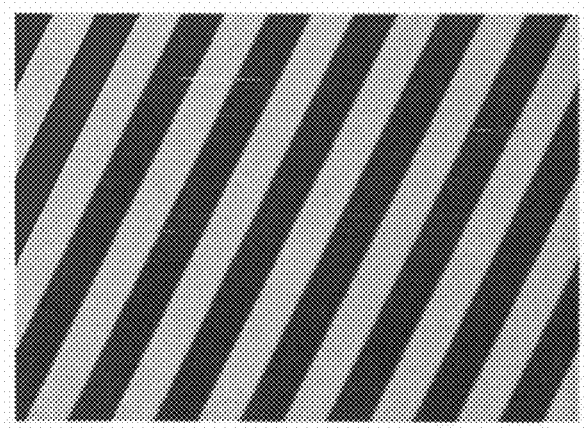
FIG. 29 shows a measurement result image when S-polarized light component entered the optical filter of FIG. 28.

FIG. 29 shows an image of measurement results when the S-polarized light component entered to the optical filter 2 of example 3 shown in FIG. 28. The optical filter 2 was prepared by setting one stripe size for about 6 μm, and the wire-grid areas and no-wire-grid areas are formed on a glass plate, wherein the wire-grid areas were used as the polarization area 2c, and the no-wire-grid areas were used as the light passing area 2a. The measurement was conducted by attaching a monochrome image intensity camera on a back face (or light-exiting face) of the optical filter 2. The light of S-polarized light component was irradiated to the optical filter 2, and the monochrome image intensity camera captured the light that passed the optical filter 2.

In FIG. 29, the black area is an area that the light was shielded. As shown in FIG. 29, it can be confirmed that the S-polarized light component is effectively shielded at the polarization area 2c where the wire grid is formed.

The above described optical filters 2 can be disposed in front of the image sensor 4 as shown in FIG. 19. Specifically, the optical filter 2 is disposed and fixed near the image sensor 4 while facing the concave/convex structure face of the optical filter 2 to the light receiving face of the image sensor 4.

The optical filter 2 can be fixed near the image sensor 4 by using known fixing methods. For example, a spacer is disposed around the light receiving face of the image sensor 4 to fix the optical filter 2 thereon, or an adhesive agent can be filled between the concave/convex structure face of the optical filter 2 and the image sensor 4 to bond the optical filter 2 and the image sensor 4. As for the bonding method, the light passing performance of adhesive agent is low compared to an air layer. Therefore, to secure the light passing performance same as the air layer, a high aspect ratio structure is required when the adhesive agent is filled between the optical filter 2 and the image sensor 4, which results into a complication of manufacturing process.

Further, the optical filter 2 can be fixed to the image sensor 4 as follows. The image sensor 4 is attached on the sensor base 3 such as a printed wiring board (PWB) by a wire bonding, and then the optical filter 2 is fixed on the sensor base 3, or the optical filter 2 and the image sensor 4 are fixed each other, and then such optical filter 2 and image sensor 4 are installed on the PWB. Manufacturing cost can be reduced by bonding the wafer of image sensor 4 and the wafer of optical filter 2 at first, and then dicing such wafers.

The RAW image data, output from the optical filter camera 210, includes bright image data and dark image data. The bright image data is stored in the bright area image memory 211, and the dark image data is stored in the dark area image memory 212. When the bright image data and dark image data are input to the monochrome image processor 221, the monochrome image processor 221 computes monochrome image intensity for each of unit processing areas, wherein one unit processing area is composed of adjacent two pixels using one pixel for the bright image data and the other pixel for the dark image data.

Specifically, the monochrome image processor 221 computes the monochrome image intensity for each of the unit processing areas by adding the bright image intensity value I1 and the dark image intensity value I2 for each of the unit processing areas, by which the monochrome image intensity is computed as a total of "I1+I2."

The monochrome image intensity data computed by the monochrome image processor 221 is transmitted to the subsequent devices and used as, for example, visual information to be output or displayed on a display device such as LCD, or information for object identification processing. In an example embodiment, the monochrome image data is used by an object identification unit 27 (see FIG. 18) for an object identification processing, as described later.

The bright image data stored in the bright area image memory 211 and dark image data stored in the dark area image memory 212 are also input to a spectroscopic image processor 222 (see FIG. 18). The spectroscopic image processor 222 computes the contrast index value indicating the contrast strength of bright image and dark image for each one of the unit processing areas using the bright image data and dark image data. In an example embodiment, a correlation between the contrast index value at the unit processing area and light wavelength entering the unit processing area is used, to generate, for example, a spectroscopic image data, in which the difference of the contrast index value can be expressed by the difference of gradient.

A description is given of a generation method of spectroscopic image data using a contrast index value with reference to the following first and second methods of spectroscopic image generation.

(First Example Method of Spectroscopic Image Generation)

A description is given of a generation method of spectroscopic image data (first method of spectroscopic image generation), in which the optical filter 2 having the light passing area 2a and the light shielding area 2b alternatively arranged next to each other two-dimensionally (i.e., grid pattern of checkerboard pattern) is used.

Figure 30:
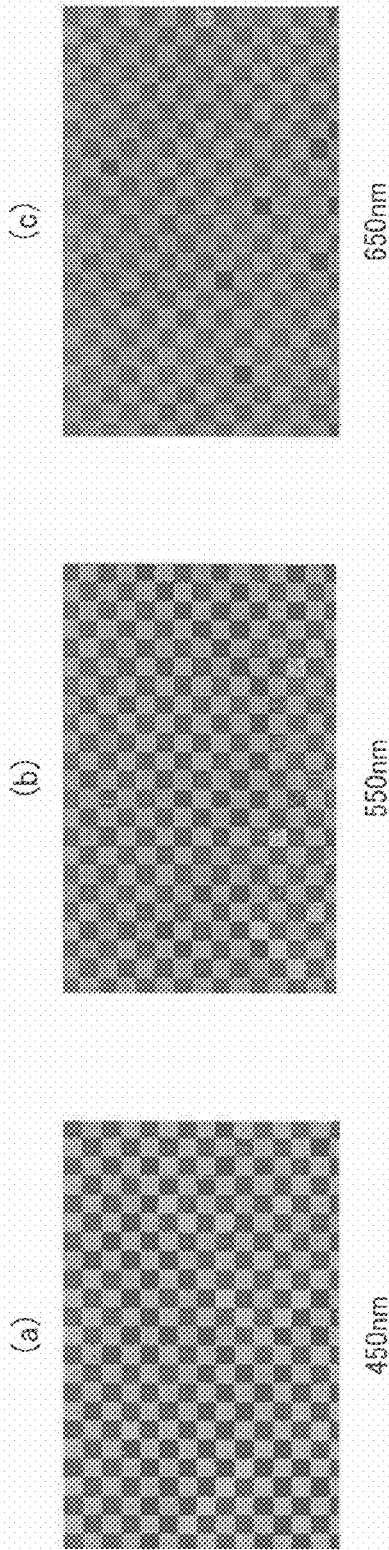
FIGS. 30(a), 30(b), and 30(c) show photographic views of captured image output from a signal processer when three light wavelength (450 nm, 550 nm, 650 nm) entered for first method of spectroscopic image generation.

FIGS. 30(a), 30(b), and 30(c) show photographic views of captured image (RAW image) output from the signal processor 5 when the incident light of three wavelengths such as 450 nm, 550 nm, and 650 nm entered the optical filter 2. The light passing area 2a and the light shielding area 2b of the optical filter 2 form a grid pattern, which is an area-divided pattern, and each of the light passing area 2a and the light shielding area 2b corresponds to each pixel in the image sensor 4 as one-to-one basis, and the pattern of bright image and dark image of the captured image corresponds to the pixel pattern.

As shown in FIGS. 30(a), 30(b), and 30(c), it can be confirmed that the contrast of bright image and dark image of the captured image changes when the wavelength of incident light changes. Further, the incident light of three wavelengths such as 450 nm, 550 nm, and 650 were prepared by passing a white light through a band pass filter. The band pass filter passes light with a given wavelength-passing-window for each of intended wavelength. Specifically, the band pass filter passes the light of 650 nm, 550 nm, and 450 nm with a wavelength-passing-window of ±40 nm.

The contrast of bright image and dark image of captured image differs depending on the wavelength of incident light, in which such difference occurs by the grid pattern of the optical filter 2, and the optical property related to the arrangement of the optical filter 2 and the image sensor 4. Such optical property includes a spectroscopy light passing ratio, a dispersion phenomenon of light, and a diffraction phenomenon of the optical filter 2, in which the diffraction phenomenon effect with respect to the grid pattern of the optical filter 2 may be a main factor of optical property that affects the contrast of bright image and dark image.

When the diffraction phenomenon occurs, the light flux passing one light passing area 2a reaches a pixel corresponding to such one light passing area 2a, and also reaches to one or more adjacent pixels due to the diffraction phenomenon of light. The diffraction phenomenon has the wavelength-dependency, in which the longer the wavelength, the greater the angle of diffraction. Therefore, the longer the wavelength of light passing the light passing area 2a, the smaller the light amount received by the pixel corresponding to the light passing area 2a and the greater the light amount received by adjacent pixels existing adjacent to the pixel corresponding to the light passing area 2a.

Therefore, the longer the wavelength of light passing the light passing area 2a, the smaller the difference of received light intensity between the pixel corresponding to the light passing area 2a and the adjacent pixels corresponding to the light shielding area 2b, in which the contrast of bright image and dark image of captured image becomes low.

Figure 31:
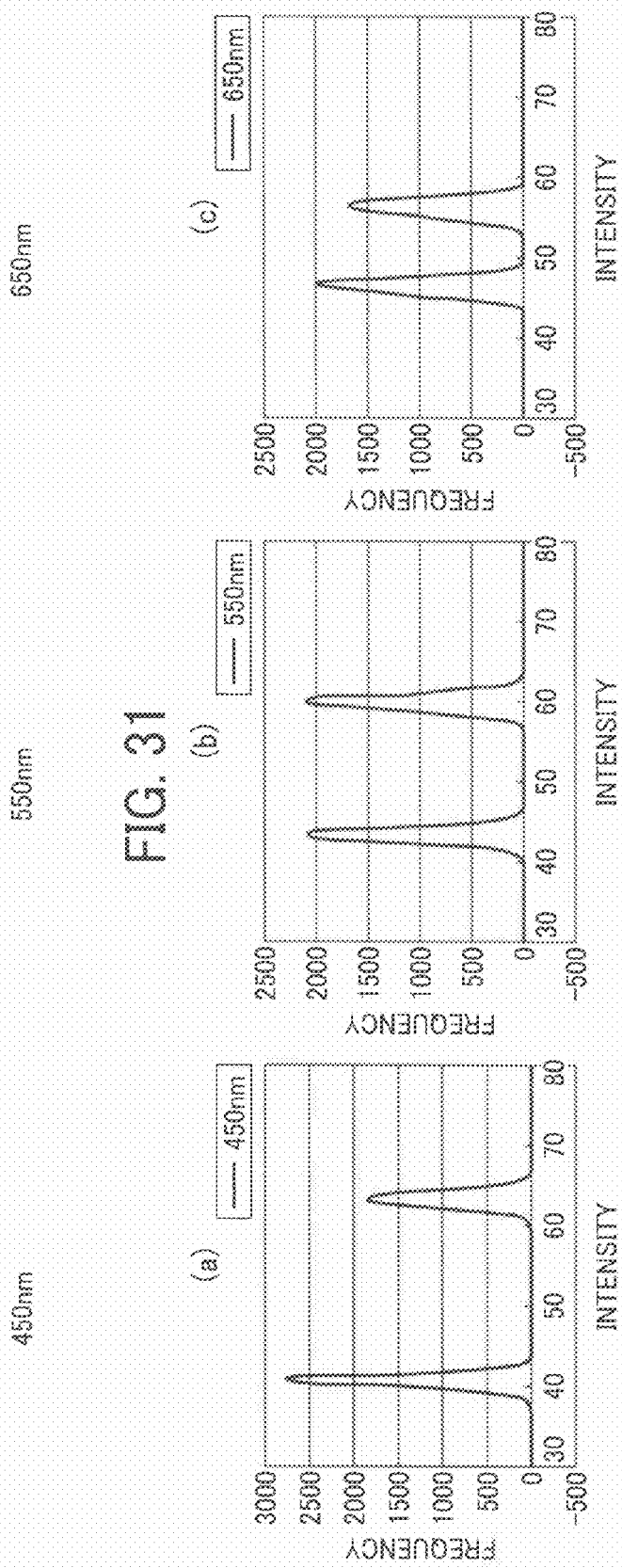
FIGS. 31(a), 31(b), and 31(c) show histograms of received light intensity for each pixel of the image sensor 4 when the incident light of three wavelengths such as 450 nm, 550 nm, and 650 nm entered for first method of spectroscopic image generation.

FIGS. 31(a), 31(b), and 31(c) show histograms of received light intensity or light intensity value for each pixel of the image sensor 4 when the incident light of three wavelengths such as 450 nm, 550 nm, and 650 nm entered the optical filter 2. As shown in FIGS. 31(a), 31(b), and 31(c), the peak value can be observed at a pixel (dark image pixel) corresponding to the light shielding area 2b, and at a pixel (bright image pixel) corresponding to the light passing area 2a.

The peak value of pixel correlating to the light shielding area 2b (dark image pixel) has a low light intensity value, and the peak value of pixel correlating to the light passing area 2a (bright image pixel) has a high light intensity value. However, the difference of light intensity between such two peak values differs depending on the wavelength of light that passed the optical filter 2. Specifically, the longer the wavelength of light that passed the optical filter 2, the smaller the difference of light intensity difference between the two peaks.

The contrast between the bright image and the dark image can be expressed by an index value using the bright image intensity value I1 and dark image intensity value I2. For example, the difference value of "I1−I2" between the bright image intensity value I1 and dark image intensity value I2 can be used as the index value.

In the example embodiment, the contrast index value Ic, expressed by the following calculation formula (8) can be used, in which the difference of "I1−I2" is divided by the total of the light intensity of "I1+I2." Therefore, the contrast index value Ic, which indicates the contrast between the bright image and the dark image for the unit processing area is expressed as a ratio of the difference of "I1−I2," which is between the bright image intensity value I1 and dark image intensity value I2, and the total of light intensity composed of the bright image intensity value I1 and the dark image intensity value I2.

$$Ic = (I1 - I2)/(I1 + I2) \qquad (8)$$

Further, the contrast index value Ic can be also construed as a difference between a ratio of the bright image intensity value I1 with respect to the total of light intensity (I1+I2) and a ratio of the dark image intensity value I2 with respect to the total of light intensity (I1+I2).

Figure 32:
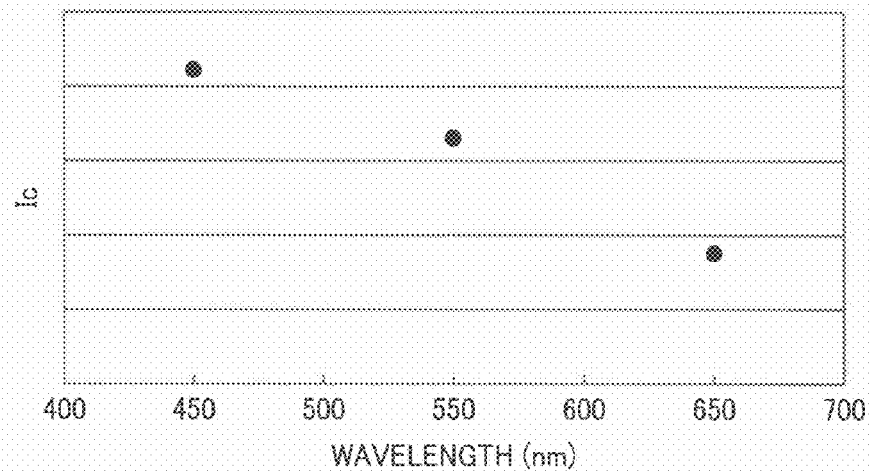
FIG. 32 show graphs of contrast index value Ic for captured image when the incident light of three wavelengths such as 450 nm, 550 nm, and 650 nm entered an optical filter for first method of spectroscopic image generation.

FIG. 32 show a graph of the contrast index value Ic for captured image when the incident light of three wavelengths such as 450 nm, 550 nm, and 650 nm entered the optical filter 2. As shown in FIG. 32, it can be confirmed that the contrast index value Ic has a wavelength-dependency. Therefore, by computing the contrast index value Ic, indicating the difference of light intensity between the pixel for bright image and the pixel for dark image, the wavelength of light entering the pixels can be computed.

In an example embodiment, each of the adjacent two pixels is corresponded to the bright image and dark image (one for bright image, and the other for dark image). Therefore, by computing the contrast index value Ic of such adjacent two pixels, the wavelength of light entering the adjacent two pixels can be determined. Therefore, by computing the contrast index value Ic of the adjacent two pixels for the entire captured image and plotting the contrast index value Ic of the adjacent two pixels at a position for each of the adjacent two pixels, a two-dimensional distribution profile of the contrast index value Ic can be prepared.

In such two-dimensional distribution profile, each point in the image capturing area correlates to the wavelength measured at each point. Therefore, if the two-dimensional distribution profile is, for example, displayed as an image expressed by the difference of gradient (which may be referred to as difference-value-based image), corresponding the difference of the contrast index value Ic, the two-dimensional distribution profile can be prepared and used as a spectroscopic image.

(Second Example Method of Spectroscopic Image Generation)

A description is given of another generation method of spectroscopic image data (second method of spectroscopic image generation), in which the optical filter 2 having the light passing area 2a and the light shielding area 2b alternatively arranged next to each other in two-dimensional directions (i.e., grid pattern of checkerboard pattern) is used.

In the above described first method of spectroscopic image generation, the contrast index value is expressed as Ic=(I1−I2)/(I1+I2) as shown by the calculation formula (8). In the second method of spectroscopic image generation, the contrast index value is expressed as SPc as shown by the calculation formula (9).

$$SPc=(S-P)/(S+P) \quad (9)$$

In the calculation formula (9), "P" is the light intensity of P-polarized light component passing the polarization area 2c. Specifically, "P" is the received light intensity value of one pixel, corresponding to the polarization area 2c that can pass through P-polarized light component but shields S-polarized light component. "S" is the light intensity of S-polarized light component passing the light passing area 2a. The "S" can be computed by subtracting the "P" (light intensity value of pixel corresponding to the polarization area 2c) from the light intensity value of pixel corresponding to the light passing area 2a.

Figure 33:
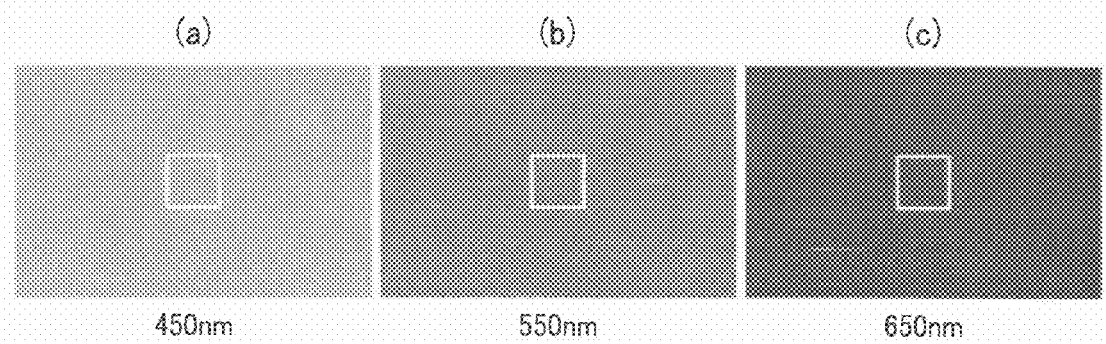
FIGS. 33(a), 33(b), and 33(c) show photographic views of captured image output from the signal processor 5 when the incident light of three wavelengths such as 450 nm, 550 nm, and 650 nm entered an optical filter for second method of spectroscopic image generation.
Figure 34:
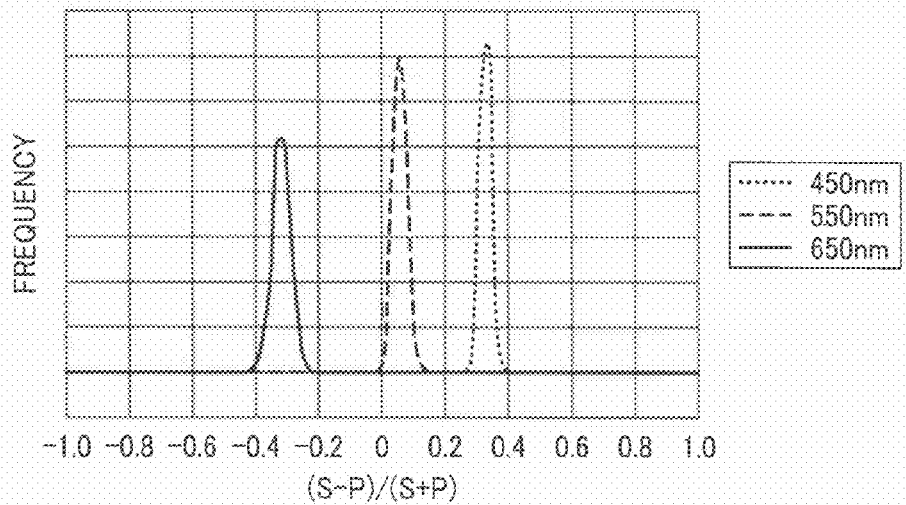
FIG. 34 shows histogram of measurement result of distribution of contrast index value obtained at the enclosed areas in FIGS. 33(a), 33(b), and 33(c)

FIGS. 33(a), 33(b), and 33(c) show photographic views of captured image (RAW image) output from the signal processor 5 when the incident light of three wavelengths such as 450 nm, 550 nm, and 650 nm entered the optical filter 2. FIG. 34 shows histogram of measurement result of distribution of the contrast index value SPc=(S−P)/(S+P) obtained at the enclosed areas, indicated by lines in FIGS. 33(a), 33(b), and 33(c).

As shown in FIG. 34, the contrast index value SPc has a wavelength-dependency. Specifically, the longer the light wavelength, the more shift to the minus direction of the contrast index value SPc. Therefore, by computing the contrast index value SPc using the light intensity value of adjacent two pixels, the wavelength of incidence light entering the adjacent two pixels can be determined. Therefore, by computing the contrast index value SPc of the adjacent two pixels for the entire captured image and plotting the contrast index value SPc of the adjacent two pixels at a position for each of the adjacent two pixels, the two-dimensional distribution profile of the contrast index value SPc can be prepared.

In such two-dimensional distribution profile, each point in the image capturing area correlates to the wavelength measured at each point. Therefore, if the two-dimensional distribution profile is, for example, displayed as an image expressed by the difference of gradient, corresponding the difference of the contrast index value SPc, the two-dimensional distribution profile can be prepared and used as a spectroscopic image.

The histogram of FIG. 34 is shown by setting the range of the contrast index value SPc from −1 to +1. As for the actual image output, images are expressed, for example, with 256 gradients (i.e., 256 different gradients), in which +1 of the histogram can be set as black, and −1 of the histogram can be set as white, by which a spectroscopic image having a gray scale of 256 gradients can be obtained. By viewing such spectroscopic image, the spectroscopy condition of the image capturing area (i.e., two-dimensional distribution profile of wavelength) can be recognized as visual information. Further, a color table corresponding to the wavelength can be used, as required.

Figure 35:
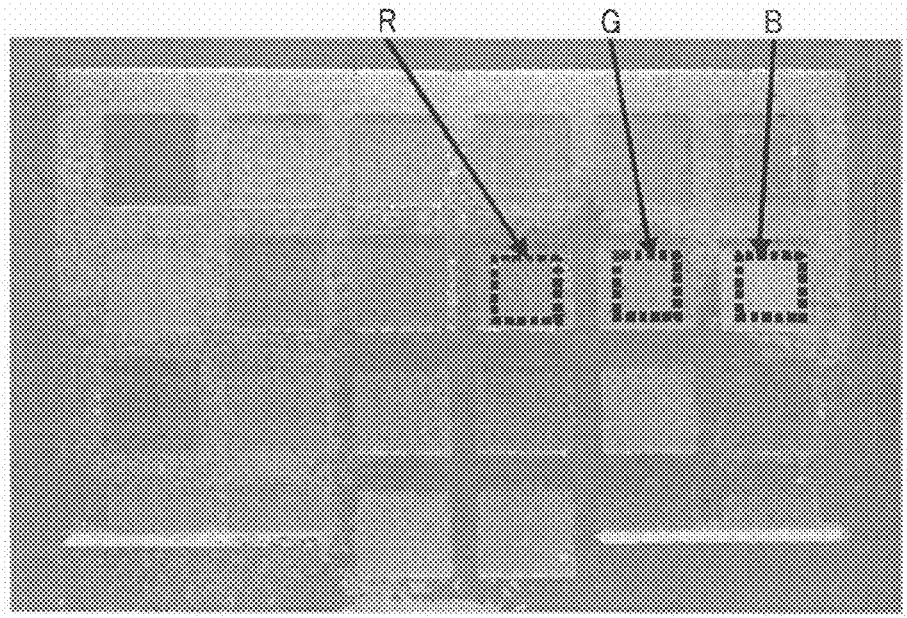
FIG. 35 shows a spectroscopic image, which was obtained by capturing a color chart and based on the contrast index value.
Figure 36:
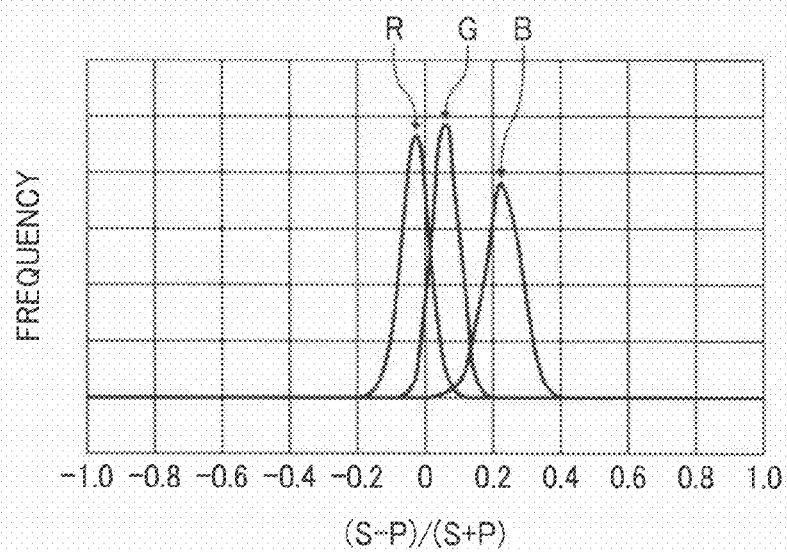
FIG. 36 shows histogram of measurement results of distribution of the contrast index value at R, G B shown in FIG. 35.

FIG. 35 shows a spectroscopic image, which was obtained by capturing a color chart, available at the market, using the optical filter camera 210 and based on the contrast index value SPc. In FIG. 35, "R" indicates a red part, "G" indicates a green part, and "B" indicates a blue part. FIG. 36 shows histogram of measurement result of distribution of the contrast index value SPc=(S−P)/(S+P) of R, G, B parts shown in FIG. 35. As shown in the spectroscopic image of FIG. 35, it can be confirmed that the difference of colors (or difference of wavelengths) appeared as the difference of gradient. Further, as shown in the histogram of FIG. 36, it can be confirmed that the difference of colors (or difference of wavelengths) appeared as the difference of the contrast index value SPc.

Therefore, by computing the contrast index value SPc using the light intensity value of adjacent two pixel, the difference of the contrast index value SPc can be expressed as a spectroscopic image having difference of gradient as shown in FIG. 35, by which the two-dimensional spectroscopic image corresponding each point in the image capturing area with the measured wavelength can be prepared and used.

The data of the contrast index value, obtained by conducting the above described spectroscopic image processing by using the spectroscopic image processor 222, may be referred to as spectroscopic image data. When the spectroscopic image data is transferred to a wavelength obtaining unit 223, the wavelength obtaining unit 223 conducts a process to obtain spectroscopy condition information of each part in the image capturing area based on the input spectroscopic image data, in which the wavelength obtaining unit 223 determines the wavelength of light coming from each part in the image capturing area.

Such spectroscopy condition information is transmitted to a noise parameter estimation unit 225 (see FIG. 18), and the noise parameter estimation unit 225 determines a noise removing parameter suitable for a specific area or an all area in the spectroscopic image using the spectroscopy condition information.

A parameter storage 224 (see FIG. 18), usesable as a parameter storage unit, stores the noise removing parameters, by which noise components in an image area can be removed with a high precision. The noise removing parameters to be used for removing the noise components can be set for each of a plurality of wavelengths, which may appear in a spectroscopic image. In an example embodiment, as described later, a noise removing method using a ε filter is employed to remove the noise component, and thereby the noise removing parameter is ε value. The parameter storage 224 stores a data table that correlates each of wavelengths and each of ε values suitable for each of wavelengths. The ε value suitable for each of wavelengths can be determined by capturing, for example, about 100 sample images of spectroscopic images and applying a noise removing filter or ε filter in advance.

The noise parameter estimation unit 225 searches the data table stored in the parameter storage 224, and reads out a noise removing parameter or ϵ value, suitable to remove a noise component included in the spectroscopic image, from the parameter storage 224 based on the spectroscopy condition information processed by the wavelength obtaining unit 223. The read-out noise removing parameter is output to a noise remover 226 used as a noise removal unit.

Figure 37:
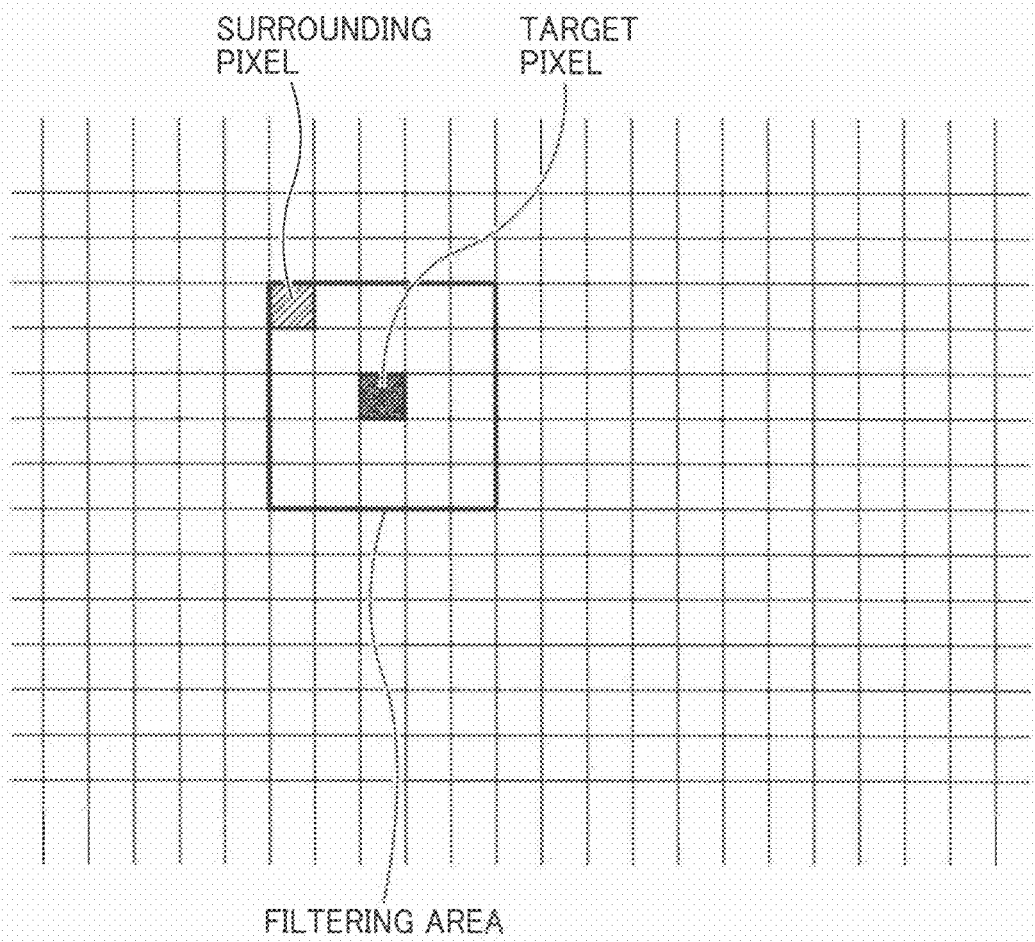
FIG. 37 shows a filtering area for a noise removing method using a ϵ filter.

The noise remover 226 conducts a noise removing processing to remove a noise component in the spectroscopic image data generated by the spectroscopic image processor 222. In an example embodiment, a noise removing method using a ϵ filter having 5×5 pixels is explained as one example with reference to FIG. 37. The window such as 5×5 pixels includes a target pixel at the center of window, and surrounding pixels existing around the target pixel. The ϵ filter can be used as follows. As shown in FIG. 37, when the noise removing is conducted for such 5×5 pixels, the absolute value of light intensity difference between the target pixel and the surrounding pixels are compared with a ϵ value (or threshold value) used as the noise removing parameter.

When the absolute value is less than the ϵ value, the light intensity data of the relevant surrounding pixels are can be used for the averaging process. In contrast, when the absolute value is greater than the ϵ value, it is determined that the light intensity data of relevant surrounding pixels are noise, and not used for the averaging process. By conducting such noise removing method, the surrounding pixels having a light intensity value, which is too different from the light intensity value of the target pixel, can be determined and removed as noise using the ϵ filter.

In the noise removing processing of an image having noise, if the ϵ value used as a threshold value is set to a great value, the noise can be removed with a great amount. However, if the ϵ value is set to a high value, an edge component defining a boundary of an identification target object may be removed as noise with a high probability, by which the edge component that needs to be maintained as the captured image after removing the noise may decrease. Therefore, when conducting the noise removing processing, the ϵ value or threshold value needs to be adjusted to a suitable value in view of noise component and edge component.

Further, as for other noise removing methods not using the ϵ filter such as a noise removing method using a bilateral filter, a wavelet conversion, or the like, the determination of noise removing parameter for the noise removing processing is also important. In this disclosure, the "noise removing processing" means an image processing for reducing or removing noise from captured image data or spectroscopic image data, which may include noise. Therefore, in this disclosure, "noise removing" means removing noise from spectroscopic image data completely and reducing noise from spectroscopic image data.

An object identification unit 227 (see FIG. 18) conducts an object identification processing for an image capturing area using monochrome image data output from the monochrome image processor 221, and the spectroscopic image data having removed the noise component by the noise remover 226.

When the object identification processing is used for operator support system according to an example embodiment, the optical filter camera 210, mounted in automobile, captures an image of forward direction of automobile moving in one direction, and obtains a spectroscopic image. Based on the spectroscopic image, an incoming automobile or another automobile in front of his automobile and/or obstacles at the shoulder of a road can be recognized.

Further, the object identification processing can be applied other purposes. For example, the object identification processing can be applied to factory automation (FA), in which the optical filter camera 210 captures parts being conveyed on a factory line, and obtains a spectroscopic image. Based on the spectroscopic image, the conveyed parts can be picked by a picking device at a given timing.

In an example embodiment, the object identification processing can be conducted using the monochrome image and the spectroscopic image data, in which the object identification can be conducted using information of wavelength or color reflected from an object, and thereby the identification of object can be conducted with a high precision compared to using only monochrome image. Further, because the noise component is removed from the spectroscopic image data, the object identification can be conducted with a further high precision.

Figure 38:
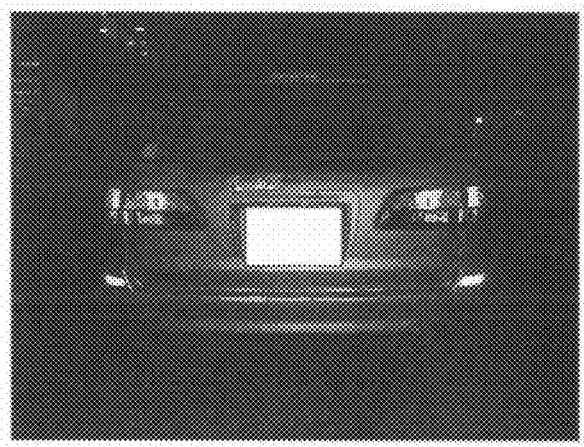
FIG. 38 shows an image captured by an optical filter camera of an operator support system mounted in an automobile, in which a back image of automobile in front of one automobile was captured at night.
Figure 39:
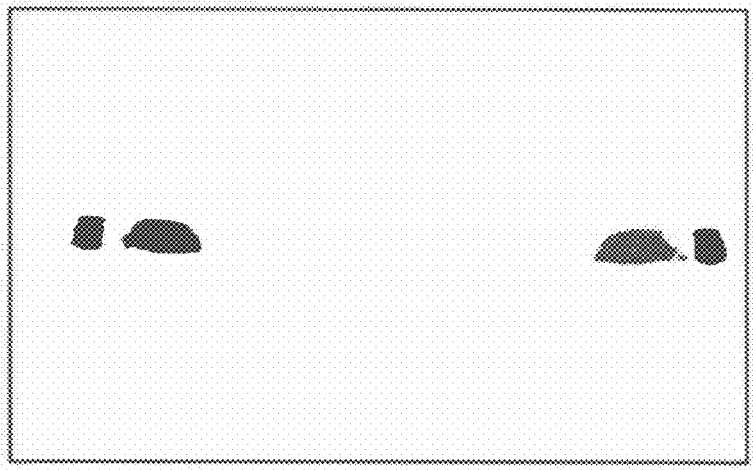
FIG. 39 shows a spectroscopic image of same image capturing area of FIG. 38 without a noise removing processing.
Figure 40:
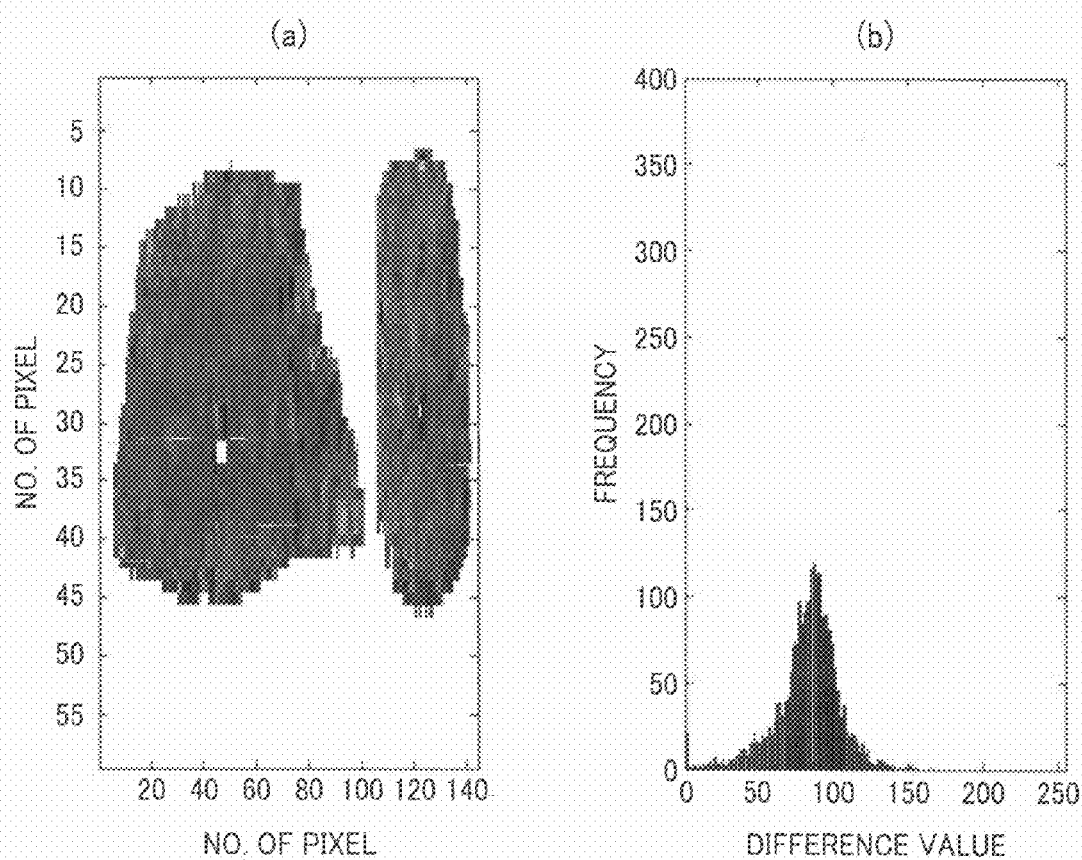
FIG. 40(a) shows an expanded view of image data of tail lamp at one side shown in the spectroscopic image of FIG. 39.
FIG. 40(b) shows a histogram of difference of "I1−I2" corresponding to a case of FIG. 40(a)

A description is given of example result of the noise removing processing conducted by the noise remover 226. FIG. 38 shows an image captured by the optical filter camera 210 of the operator support system mounted in an automobile, in which a back image of automobile in front of one automobile was captured at night. FIG. 39 shows a spectroscopic image of same image capturing area of FIG. 38 captured by the optical filter camera 210. In the spectroscopic image shown in FIG. 39, by conducting an exposure adjustment, only the tail lamps of the in-front automobile are extracted. FIG. 40(a) shows an expanded view of image data of the tail lamp at one side shown in the spectroscopic image of FIG. 39, and FIG. 40(b) shows a histogram of difference of "I1−I2" corresponding to a case of FIG. 40(a). It should be noted that data of FIG. 39, FIG. 40(a), and FIG. 40(b) are data that the noise removing process was not conducted.

Figure 41:
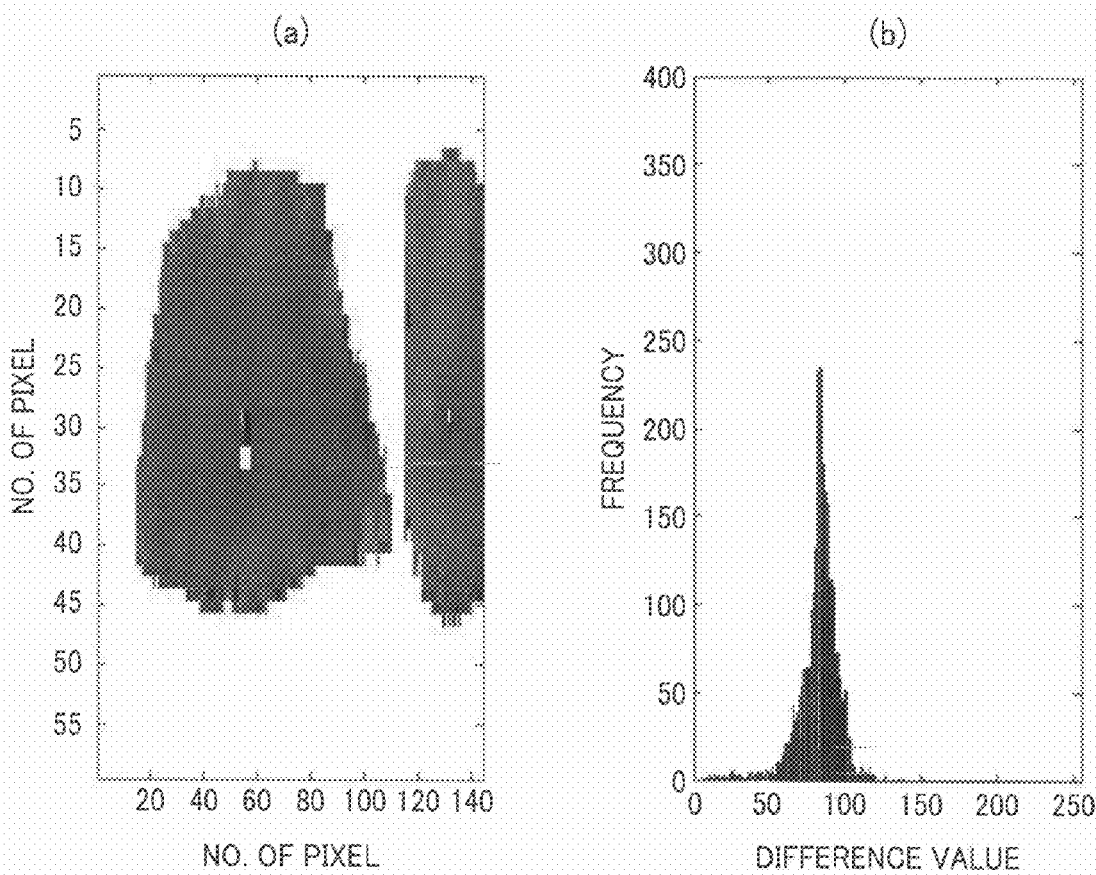
FIG. 41(a) shows an expanded view of image data of tail lamp at one side shown in the spectroscopic image of FIG. 39, to which the noise removing processing according to an example embodiment was conducted.
FIG. 41(b) shows a histogram of difference of "I1−I2" corresponded a case of FIG. 41(a)

FIG. 41(a) shows an expanded view of image data of the tail lamp at one side shown in the spectroscopic image of FIG. 39, to which the noise removing processing according to an example embodiment was conducted, and FIG. 41(b) shows a histogram of difference of "I1−I2" corresponding to a case of FIG. 41(a).

As shown in FIG. 41(b), when the noise removing processing was conducted, the distribution width of difference of "I1−I2" becomes narrower than the distribution width of difference of "I1−I2" shown in FIG. 40(b) not conducted with the noise removing processing. Therefore, it can be understood that the noise was effectively removed from the spectroscopic image data by conducting the noise removing processing according to an example embodiment.

Figure 42:
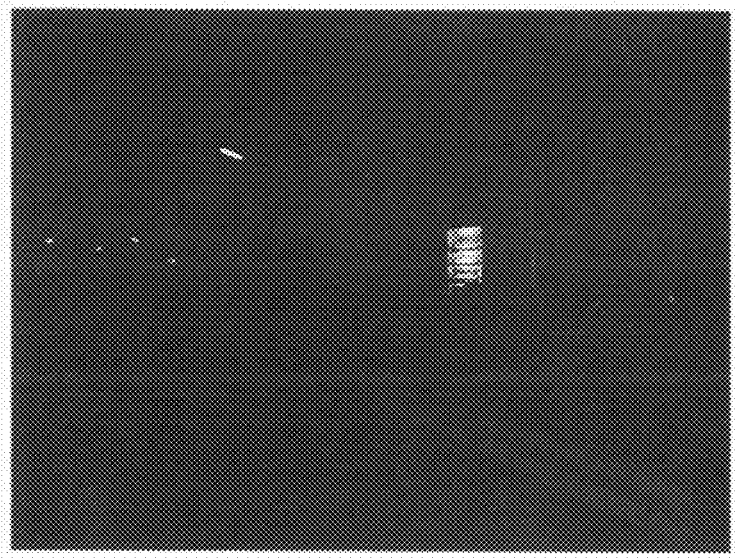
FIG. 42 shows an image captured by an optical filter camera of an operator support system mounted in an automobile, in which an automatic vending machine disposed at a road side-end was captured at night.
Figure 43:
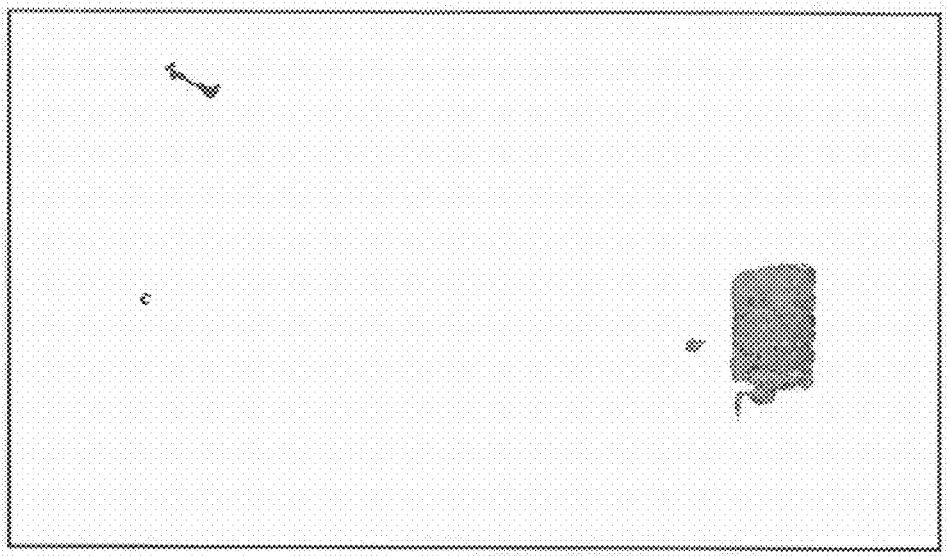
FIG. 43 shows a spectroscopic image of same image capturing area of FIG. 42 without a noise removing processing.
Figure 44:
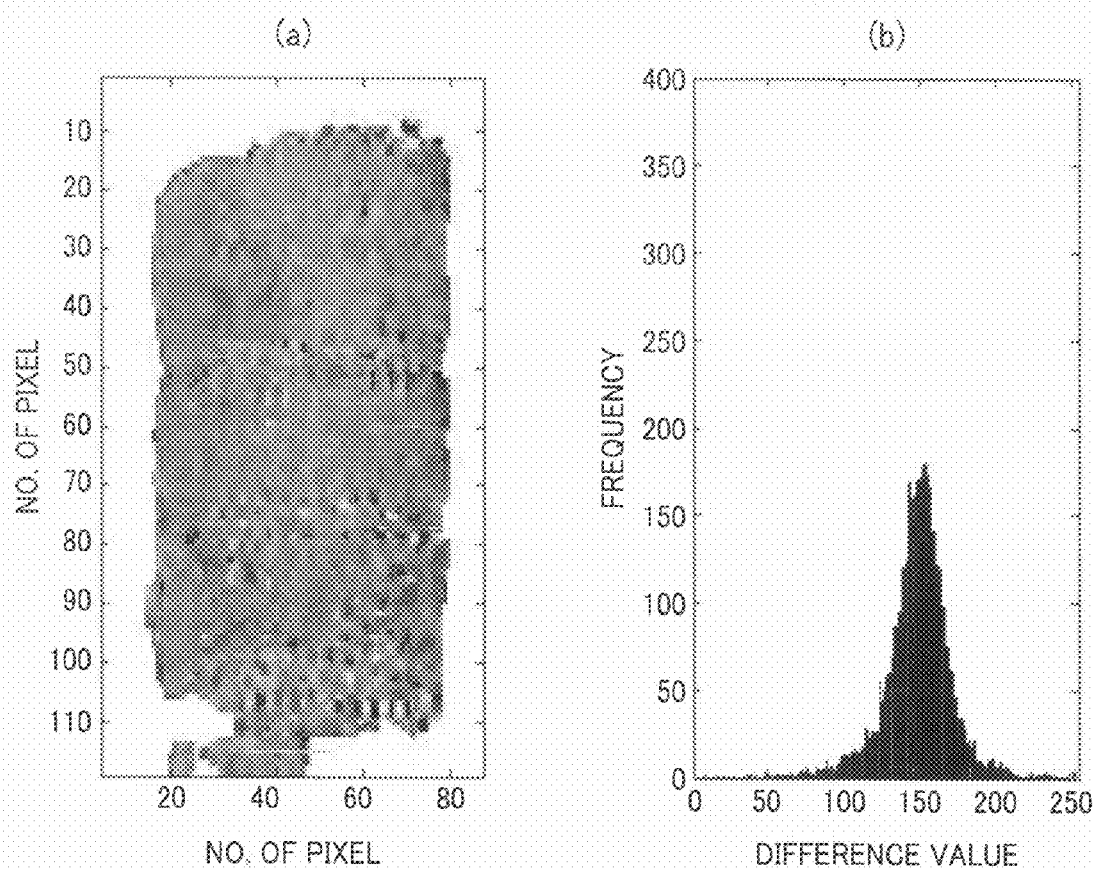
FIG. 44(a) shows an expanded view of image data of the automatic vending machine shown in the spectroscopic image of FIG. 43.
FIG. 44(b) shows a histogram of difference of "I1−I2" corresponding to a case of FIG. 44(a)

A description is given of another example result of the noise removing processing conducted by the noise remover 226. FIG. 42 shows an image captured by the optical filter camera 210 of the operator support system mounted in an automobile, in which an automatic vending machine (ATM) disposed at a road side-end was captured at night. FIG. 43 shows a spectroscopic image of same image capturing area of FIG. 42 captured by the optical filter camera 210. In the spectroscopic image shown in FIG. 43, by conducting an exposure adjustment, only the ATM was extracted. FIG. 44(a) shows an expanded view of image data of the ATM shown in the spectroscopic image of FIG. 43, and FIG. 44(b) shows a histogram of difference of "I1−I2" corresponding to a case of FIG. 44(a). It should be noted that data of FIG. 43, FIG. 44(a), and FIG. 44(b) are data that the noise removing process was not conducted.

Figure 45:
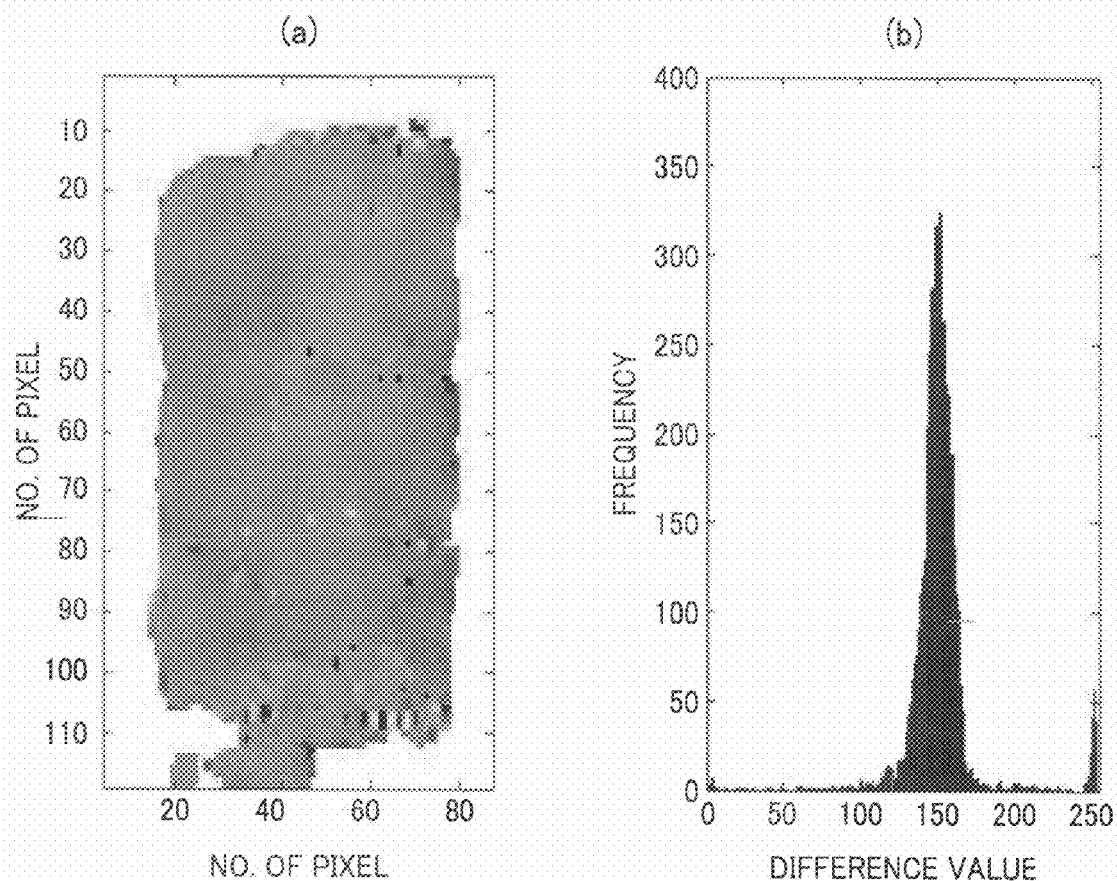
FIG. 45(a) shows an expanded view of image data of the automatic vending machine shown in the spectroscopic image of FIG. 43 to which the noise removing processing according to an example embodiment was conducted.
FIG. 45(b) shows a histogram of difference of "I1−I2" corresponding to a case of FIG. 45(a).

FIG. 45(a) shows an expanded view of image data of the ATM shown in the spectroscopic image of FIG. 43 to which the noise removing processing according to an example embodiment was conducted, and FIG. 45(b) shows a histogram of difference of "I1−I2" corresponding to a case of FIG. 45(a).

As shown in FIG. 45(b), when the noise removing processing was conducted, the distribution width of difference of "I1−I2" is becomes narrower than the distribution width of difference of "I1−I2" shown in FIG. 44(b) not conducted with the noise removing processing. Therefore, it can be understood that the noise was effectively removed from the spectroscopic image data by conducting the noise removing processing according to an example embodiment.

As for the operator support system according to an example embodiment, by conducting the object identification processing using the spectroscopic image data, the tail lamp of the in-front automobile and the ATM can be identified based on the difference of wavelengths of lights coming from the tail lamp and ATM.

Then, the object identification result can be suitably used, for example, for controlling the light orientation of head lamp of a vehicle. When each of objects are identified, the head lamp direction can be changed such as the light beam is not directed to the incoming automobile or in-front automobile while the light beam is directed to other objects effectively.

When comparing the histogram data of FIG. 40(b) and FIG. 44(b), not conducted with the noise removing processing, the distribution of histogram of FIG. 40(b) and the distribution of histogram of FIG. 44(b) overlaps each other at some portions. Therefore, the tail lamp of in-front automobile and the ATM at the road side-end may not be differentiated and identified with a high precision.

In contrast, when comparing the histogram data of FIG. 41(b) and FIG. 45(b), conducted with the noise removing processing, the distribution of histogram of FIG. 41(b) and the distribution of histogram of FIG. 45(b) do not substantially overlap each other. Therefore, the tail lamp of in-front automobile and the ATM at the road side-end can be differentiated and identified with a high precision.

The spectroscopic image capturing apparatus according to an example embodiment can obtain a two-dimensional spectroscopic image which correlates each point in a given image capturing area with wavelength information measured at the each point, in which light coming from an image capturing area is detected by the image sensor 4 having a two-dimensionally arranged pixel array, via the optical filter 2, and the detection result is output from the image sensor 4. The optical filter 2 may employ a diffraction grating having a grid pattern correlating to a unit area of the image sensor 4, wherein the unit area includes one pixel or two or more pixels, which may be arranged straightly in the Y direction or in the slanted direction.

The grid width or grid area, and the distance between the optical filter 2 and the image sensor 4 can be set to given values so that the received light intensity I1 and I2 for the adjacent two unit areas becomes different, by which interference of light at each point on the image sensor 4 after passing the diffraction grating can be differentiated depending on the diffraction angle of light.

As for the spectroscopic image capturing apparatus, the contrast index value Ic=(I1−I2)/(I1+I2), which is a light intensity difference value between adjacent two unit areas, is computed based on the detection result of the image sensor 4. Then, based on the difference value of the contrast index value Ic (difference of the contrast index value Ic for the adjacent two unit areas can be expressed as the difference of gradient), the spectroscopic image processor 222 generates a spectroscopic image.

Therefore, as described with the first method of spectroscopic image generation, the two-dimensional distribution profile of the contrast index value Ic correlates each point in the image capturing area with wavelength information measured at the each point. Therefore, the difference of the contrast index value Ic can be expressed, for example, as a difference of gradient, and can be used as a spectroscopic image.

Further, the optical filter 2 may be a diffraction grating having a grid pattern alternatively arranging the polarization area 2c to shield a polarization component such as S-polarized light component, and the light passing area 2a to pass through the S-polarized light component. In this case, "P" is the received light intensity value of one pixel for one unit area corresponding to the polarization area 2c that can pass through P-polarized light component but shields S-polarized light component, and "S" is the received light intensity value for the adjacent one unit area corresponding to the light passing area 2a. Such "P" and "S" are used to compute the contrast index value SPc=(S−P)/(S+P) based on the detection result of the image sensor 4. Then, based on the computed contrast index value SPc, an image expressed by the difference of the contrast index value SPc or difference of gradient can be generated.

As described with the second method of spectroscopic image generation, a two-dimensional distribution profile of the contrast index value SPc correlates each point in an image capturing area with wavelength information measured at each point, and thereby an image expressed by the difference of the contrast index value SPc or difference of gradient can be used as a spectroscopic image.

In an example embodiment, the noise removal unit such as the noise remover 226 is employed to conduct the noise removing processing to remove noise components from a generated spectroscopic image using the noise removing parameter such as $\epsilon$ filter, by which the spectroscopic image with less noise can be obtained. By conducting such noise removing processing, the subsequent processes such as the object identification processing using such spectroscopic image can be conducted without degrading the identification precision.

Conventional noise removing methods may not remove noise component in a spectroscopic image effectively because the conventional noise removing methods may use a reference noise removing parameter (or threshold value, computing parameter) having a constant value to extract a noise component from a spectroscopic image, and such constant value may not be suitable for some wavelength included in a spectroscopic image, by which the noise cannot be removed effectively. As such, one single noise removing parameter that can be used for all wavelengths for the noise removing processing may not be obtained.

In an example embodiment, the parameter storage 224 stores noise removing parameters such as $\epsilon$ value that can remove noise component included in the spectroscopic image generated by the spectroscopic image processor 222 for a plurality of wavelengths with a high precision. The noise remover 226 reads out the $\epsilon$ value, matched to wavelength in a noise removing processing area in the spectroscopic image, from the parameter storage 224, and conducts the noise removing processing to the noise removing processing area using the $\epsilon$ value. Because the $\epsilon$ value matched to wavelength in a noise removing processing area in the spectroscopic image can be used to remove the noise component, the noise component in the spectroscopic image can be effectively removed.

In an example embodiment, the noise removing parameter is $\epsilon$ value, which is a threshold value to determine whether image data generated by the spectroscopic image processor 222 is a noise component. If a difference value between a target unit area (or target pixel) and a surrounding unit area (or surrounding pixel) surrounding the target pixel exceeds the $\epsilon$ value, an impulse noise removing processing is conducted to remove the concerned surrounding pixel as the noise component, by which the impulse noise can be effectively removed with a simple process.

Further, in the above described example embodiment, the operator support system is mounted in a vehicle, but it is not required to install all of the operator support system in the vehicle. For example, the vehicle is mounted with only the optical filter camera 210, and the rest of the operator support system is disposed remotely from the vehicle, in which a person other than the driver may monitor the driving condition of vehicle using the operator support system.

When light passes the diffraction grating, the light diffracts for a given angle. The diffraction angle of light changes as the wavelength of light changes, and the interference at each point on an image sensor changes. The light that diffracts at the diffraction grating may be a polarized light or a non-polarized light.

When the non-polarized light is used, a diffraction grating having a grid pattern, having the areas to pass the non-polarized light and the areas to shield the non-polarized light arranged alternatively, is used. When the polarized light is used, a diffraction grating, having a grid pattern having the areas to pass a specific polarization component and the areas to shield the specific polarization arranged alternatively, is used.

In the above example embodiment, a difference of interference at each point on an image sensor appears as a difference of the received light intensity between the adjacent two unit areas when the light diffracts after passing the diffraction grating. In the above example embodiment, based on the difference value of the received light intensity between the adjacent two unit areas, wavelength information of light correlated to a point corresponding to the concerned adjacent two unit areas can be identified. Therefore, the difference value of the received light intensity can be prepared as two-dimensional spectroscopic image by correlating each point in an image capturing area with wavelength information measured at the each point.

Further, the difference value expressed for each pixel may be expressed, for example, by the difference of gradient or difference of colors. Further, the difference value of the received light intensity can be expressed by the difference of gradient, or difference of colors, or can be expressed an index value, which is obtained by dividing the difference of the received light intensity of the adjacent two unit areas with a total of received light intensity of the adjacent two unit areas, and such computed value may be expressed as the difference of gradient, or difference of colors.

In the above example embodiment, the difference of the received light intensity, which can be used for generating the spectroscopic image, can be obtained by one image-capturing action. Such method described in the above example embodiment needs less processing time to obtain a spectroscopic image compared to a conventional spectroscopic image capturing apparatus using the wavelength selection filter. Further, such method described in the above example embodiment needs less processing time to obtain a spectroscopic image compared to a conventional spectroscopic image capturing apparatus using the dispersive element for image scanning and capturing, or a conventional spectroscopic image capturing apparatus using Fourier-transform spectroscopy that changes the phase difference for two light paths or two polarization components. In the above example embodiment, the noise removal unit can remove the noise component from the received light intensity, to be used for generating a spectroscopic image, by which the spectroscopic image with less noise can be obtained.

In the above example embodiment, a processing time to obtain a spectroscopic image using the spectroscopic image capturing apparatus can be shortened, and the spectroscopic image with less noise can be obtained.

In the above-described example embodiment, a computer can be used with a computer-readable program, described by object-oriented programming languages such as C++, Java (registered trademark), JavaScript (registered trademark), Perl, Ruby, or legacy programming languages such as machine language, assembler language to control functional units used for the apparatus or system. For example, a particular computer (e.g., personal computer, work station) may control an information processing apparatus or an image processing apparatus using a computer-readable program, which can execute the above-described processes or steps. Further, in the above-described exemplary embodiment, a storage device (or recording medium), which can store computer-readable program, may be a flexible disk, a compact disk read only memory (CD-ROM), a digital versatile disk read only memory (DVD-ROM), DVD recording only/rewritable (DVD-R/RW), electrically erasable and programmable read only memory (EEPROM), erasable programmable read only memory (EPROM), a memory card or stick such as USB memory, a memory chip, a mini disk (MD), a magneto optical disc (MO), magnetic tape, hard disk in a server, or the like, but not limited these. Further, a computer-readable program can be downloaded to a particular computer (e.g., personal computer) via a network such as the interne, or a computer-readable program can be installed to a particular computer from the above-mentioned storage device, by which the particular computer may be used for the system or apparatus according to an example embodiment, for example.

Numerous additional modifications and variations are possible in light of the above teachings. It is therefore to be understood that within the scope of the appended claims, the disclosure of the present invention may be practiced otherwise than as specifically described herein. For example, elements and/or features of different examples and illustrative embodiments may be combined each other and/or substituted for each other within the scope of this disclosure and appended claims.

What is claimed is:

1. An object identification device, comprising: an image capturing device to receive polarized light polarized in two different directions included in light reflected from an object in an image capturing area and capture two polarized images, one polarized image for each type of polarized light; circuitry configured to:

remove a noise component included in each of the two polarized images captured by the image capturing device, using a noise removing parameter;

divide each of the two polarized images captured by the image capturing device into identification-processing areas to compute an object identification index value for each of the identification-processing areas using light intensity data of each of the two polarized images from which the noise component is removed by the circuitry;

conduct an object identification process that determines a plurality of identification processing areas corresponding to an identification target object based on the object identification index value of each of the identification processing areas computed by the circuitry, and identify a plurality of adjacent identification processing areas as the identification processing areas corresponding to the identification target object as an image area of the identification target object;

obtain environment information to determine an environmental condition of an object in an image capturing area; and determine an environmental condition of the object in the image capturing area based on the environment information obtained by the circuitry; and a memory to store one or more noise removing parameters to remove a noise component included in the two polarized images captured under an environmental condition determined by the circuitry, each of the one or more noise removing parameters being specifically prepared and stored, respectively, for each one of a plurality of mutually exclusive environmental conditions, wherein the circuitry is configured to read out a specific noise removing parameter for the environmental condition determined by the circuitry from the memory, and to conduct a noise removing process using the specific noise removing parameter, and wherein the specific noise removing parameter set for each of the environmental conditions and stored in the memory is obtained by taking a plurality of polarized light sample images and obtaining two polarized images for a plurality of image capturing areas under one environmental condition and adjusting to a value to remove a noise component in the two polarized images captured under the environmental condition when conducting the noise removing process.

2. The object identification device of claim 1, wherein the specific noise removing parameter is a threshold value to determine whether light intensity data included in the two polarized images is a noise component, wherein the noise removing process comprises determining whether the light intensity data included in the two polarized images captured by the image capturing device is a noise component based on the threshold value specified by the specific noise removing parameter, and removing the light intensity data identified as a noise component from computation of the object identification index value by the circuitry.

3. The object identification device of claim 2, wherein a light intensity difference between a target pixel and surrounding pixels surrounding the target pixel in the two polarized images that exceeds the threshold value specified by the specific noise removing parameter causes an impulse noise removing process to identify the light intensity data of the surrounding pixels as a noise component and remove the light intensity data of the surrounding pixels.

4. The object identification device of claim 3, wherein, after conducting the impulse noise removing process, the noise removing process comprises removing high-frequency noise included in light intensity data in the noise removing processing area defined by the target pixel and the surrounding pixels based on light intensity data of the target pixel and light intensity data of the surrounding pixels surrounding the target pixel in the two polarization images.

5. The object identification device of claim 1, wherein the object identification index value employs a polarized light ratio for each of the identification processing areas that is a ratio of light intensity data between two polarized images captured by the image capturing images.

6. The object identification device of claim 1, wherein the object identification index value employs a polarization intensity difference for each of the identification processing areas that is a ratio between a difference in light intensity between the two polarized images and a total light intensity of the two polarized images captured by the image capturing device.

7. The object identification device of claim 6, wherein the circuitry is configured to obtain the object identification index value, computed by the circuitry, as the environment information, and to determine an environmental condition of an object in an image capturing area based on the object identification index value obtained by the circuitry.

8. The object identification device of claim 7, wherein the circuitry is configured to determine an environmental condition of an object in an image capturing area based on a variation among object identification index values measured at a plurality of points in the image capturing area.

9. A moving object control apparatus, comprising:
the object identification device according to claim 1; and
movement control circuitry configured to conduct movement control of the moving object using an identification result produced by the object identification device according to claim 1.

10. An information presenting apparatus, comprising:
the object identification device according to claim 1 to capture scenes surrounding a vehicle as an image capturing area to identify an object existing in the image capturing area;
useful information generating circuitry configured to generate useful information for an operator of the vehicle using an identification result of the object identification device; and
information reporting circuitry configured to report the information generated by the useful information generating circuitry to the operator.

11. A method of identifying an object, comprising:
receiving light polarized in two different polarization directions included in light reflected from an object in an image capturing area using an image capturing device and capturing a polarized image for each of the two types of polarized light using the image capturing device;
dividing each of the two polarized images captured by the image capturing device into identification processing areas to compute an object identification index value for each of the identification processing areas using circuitry using light intensity data of each of the two polarized images from which the noise component has been removed by the circuitry;
determining identification processing areas corresponding to an identification target object using the circuitry based on the object identification index value of each of the identification processing areas computed by the circuitry;
conducting an object identification process in which the circuitry identifies a plurality of adjacent identification processing areas determined as the identification processing areas corresponding to the identification target object as an image area of the identification target object;
obtaining environment information to determine an environmental condition of an object in the image capturing area using the circuitry;
determining an environmental condition of the object existing in the image capturing area based on the environment information obtained by the circuitry;
storing a plurality of noise removing parameters in a memory, each of the noise removing parameters being specifically prepared and stored, respectively, for each one of a plurality of mutually exclusive environmental conditions;

reading out one specific noise removing parameter from among the plurality of noise removing parameters stored in the memory for the environmental condition determined by the circuitry to remove a noise component included in the two polarized images captured under the environmental condition; and removing the noise component included in the two polarized images captured under the environmental condition determined by the circuitry using the specific noise removing parameter read from the memory, wherein the specific noise removing parameter set for each of the environmental conditions and stored in the memory is obtained by taking a plurality of polarized light sample images and obtaining two polarized images for a plurality of image capturing areas under one environmental condition and adjusting to a value to remove a noise component in the two polarized images captured under the environmental condition when conducting a noise removing processing.

12. An object identification device, comprising:

an image capturing device to receive polarized light polarized in two different directions included in light reflected from an object in an image capturing area and capture two polarized images, one polarized image for each type of polarized light;

circuitry configured to:
  remove a noise component included in each of the two polarized images captured by the image capturing device, using a noise removing parameter;
  divide each of the two polarized images captured by the image capturing device into identification-processing areas to compute an object identification index value for each of the identification-processing areas using light intensity data of each of the two polarized images from which the noise component is removed by the circuitry;
  conduct an object identification process that determines a plurality of identification processing areas corresponding to an identification target object based on the object identification index value of each of the identification processing areas computed by the circuitry, and identify a plurality of adjacent identification processing areas as the identification processing areas corresponding to the identification target object as an image area of the identification target object;
  obtain environment information to determine an environmental condition of an object in an image capturing area; and
  determine an environmental condition of the object in the image capturing area based on the environment information obtained by the circuitry; and a memory to store one or more noise removing parameters to remove a noise component included in the two polarized images captured under an environmental condition determined by the circuitry, each noise removing parameter being prepared and stored for one of a plurality of mutually exclusive environmental conditions, wherein the circuitry is configured to read out a specific noise removing parameter for the environmental condition determined by the circuitry from the memory, and to conduct a noise removing process using the specific noise removing parameter, wherein the specific noise removing parameter is a threshold value to determine whether light intensity data included in the two polarized images is a noise component, wherein the noise removing process comprises determining whether the light intensity data included in the two polarized images captured by the image capturing device is a noise component based on the threshold value specified by the specific noise removing parameter, and removing the light intensity data identified as a noise component from computation of the object identification index value by the circuitry, and wherein a light intensity difference between a target pixel and surrounding pixels surrounding the target pixel in the two polarized images that exceeds the threshold value specified by the specific noise removing parameter causes an impulse noise removing process to identify the light intensity data of the surrounding pixels as a noise component and remove the light intensity data of the surrounding pixels.

* * * * *